(12) United States Patent
Omura et al.

(10) Patent No.: US 7,034,005 B2
(45) Date of Patent: Apr. 25, 2006

(54) USE OF AGENT FOR SUPPRESSING INFECTION AND PROLIFERATION OF HUMAN IMMUNODEFICIENCY SYNDROME VIRUS

(75) Inventors: Satoshi Omura, Tokyo (JP); Kiyoko Akagawa, Tokyo (JP); Toshiaki Sunazuka, Chiba (JP)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 10/294,587

(22) Filed: Nov. 15, 2002

(65) Prior Publication Data

US 2003/0186900 A1 Oct. 2, 2003

(30) Foreign Application Priority Data

Mar. 7, 2002 (JP) ............................. 2002-061788
Sep. 6, 2002 (JP) ............................. 2002-261024

(51) Int. Cl.
A61K 31/70 (2006.01)
(52) U.S. Cl. ...................................................... 514/29
(58) Field of Classification Search ................ 514/29, 514/28, 25
See application file for complete search history.

(56) References Cited

U.S. PATENT DOCUMENTS

| | | | |
|---|---|---|---|
| 5,106,961 A * | 4/1992 | Kirst et al. ................... | 536/7.2 |
| 5,514,662 A | 5/1996 | Seman | |
| 5,541,193 A | 7/1996 | Kawai et al. | |
| 5,545,734 A | 8/1996 | Baker et al. | |

FOREIGN PATENT DOCUMENTS

| | | |
|---|---|---|
| EP | 0 254 534 | 1/1988 |
| EP | 1 064 942 | 1/2001 |

OTHER PUBLICATIONS

Tae-Wook Chun, Richard T. Davey Jr., Mario Ostrowski, J., Shawn Justement, Delphine Engel, James I. Mullins & Anthony, S. Fauci: Relationship between pre-existing viral reservoires and the re-emergence of plasma viremia after discontinuation of highly active anti-retroviral therapy, Nat Med 6: 757-761, 2000.

Lewis K. Schrager, M. Patricia D' Souza; Cellular and Anatomical Reservoirs of HIV-1 in Patients Receiving Potent Antiretroviral Combination Therapy, Jama 280: 67-71, 1998.

Swingler S, Mann A, Jacque J, Brichacek B, Sasseville VG, Williams K, Lackner AA, Janoff EN, Wang R, Fisher D, Stevenson M.: HIV-1 Nef mediates lymphocyte chemotaxis and activation By infected macrophages. Nat Med 5: 997-1003, 1999.

Kiyoko Akagawa, Iwao Komuro and Keiko Mochida: Deriversity of macrophage derived from monocytes, Inflammation and Immunity, vol. 8, 360-366, 2000.

Komuro, I., Keicho, N., Iwamoto, I., and Akagawa, K. S.: Human alveolar macrophages and GM-CSF-induced monocyte-derived macrophages and resistant to H2O2 via their high basal- and inducible-levels of catalase activity, J. Biol. Chem. 276: 24360-24364, 2001.

Hashimoto, S., Komuro, I., Yamada, M. Akagawa, K. S.: IL-10 inhibits GM-CSF-dependent human monocyte survival at the early stage of the culture and inhibits the generation of macrophages, J. Immunol. 167: 3619-3625, 2001.

Hashimoto, S., Yamada, M., Motoyoshi, K. and Akagawa, K. S.: Enhancement of macrophage-colony-stimulating factor-induced growth and differentiation of human monocytes by interleukin-10, BLOOD 89: 315-321, 1997.

Akagawa, K. S., Takasuka, N., Nozaki, Y., Komuro, I., Miyuki, A., Ueda, M., Naito, M. and Takahashi, K.: Generation of CD1+ Re1B+ Dendritic Cells and TRAP-positive Osteociast-like Multi- nucleated Giant Cells from Human Monocytes, BLOOD 88: 4029-4039, 1996.

Matsuda, S., Akagawa, K., Honda, M., Yokota, Y., Takabe, Y. and Takemori, T.: Suppression of HIV replication in human monocyte-derived macrophages induced by granulocyte/macrophage colony-stimulating factor, AIDS Research and Human Retroviruses, 11: 1031-1038, 1995.

Inflammation,Immunity and Macrorides Up to Date, Ed. Sup. Kihachiro Shimizu and Satoshi Omura, Ed. Shoji Kudo: Iyaku Journal, Inc. Osaka, 1996.

Nakata, K., Weiden, M., Harkin, T., Ho, D. and Rom, W. N.(1995). Low copy number and limited variability of proviral DNA in alveolar macrophages from HIV-1-infected patients: evidence for genetic differences in HIV-1 between lung and blood macrophage populations. Mol Med 1, 744-757.

* cited by examiner

*Primary Examiner*—Elli Peselev
(74) *Attorney, Agent, or Firm*—Young & Thompson

(57) ABSTRACT

The present invention relates to agent for suppressing infection and proliferation of human immunodeficiency syndrome virus (HIV-1), which infects immunocompetent cells such as macrophage or dendritic cell and causes destruction of immune system, and use of known compounds, macrolide derivatives for suppression of infection and proliferation of human immunodeficiency syndrome virus in M type macrophage derived from human monocytes. The present invention is useful for treatment of patients with HIV-1 infection by low cost chemotherapeutic agents, and in addition, is clinically used as supplement agent in HAART.

10 Claims, 25 Drawing Sheets

(A)

(B)

(A)

(B)

LTR-gag
(245 bp)

M-MΦ (HIV-1$^{\pm}$)

DMSO

EM

EM201

EM202

EM703

CAM

(A) p38-MAPK (B) ERK1/2

USE OF AGENT FOR SUPPRESSING INFECTION AND PROLIFERATION OF HUMAN IMMUNODEFICIENCY SYNDROME VIRUS

BACKGROUND OF THE INVENTION

1. Field of the Invention

The present invention relates to agent for suppressing infection and proliferation of human immunodeficiency syndrome virus (HIV-1), which infects immunocompetent cells such as macrophage or dendritic cell and causes destruction of immune system. More particularly, the present invention relates to use of agent for suppressing infection and proliferation of human immunodeficiency syndrome virus, agent of which suppresses infecting and proliferating human immunodeficiency syndrome virus to M type macrophage derived from human monocytes.

2. Description of Related Art

More than 40 million peoples have been infected with human immunodeficiency syndrome virus (HIV-1), and among them, about 5 million subjects were estimated to develop acquired immune deficiency syndrome (AIDS). AIDS is really a world wide infectious disease. Highly active antiretroviral therapy (HAART) for patients with HIV-1 has appeared in the early 1990's. As a result of application in the clinical field, large therapeutic effect was obtained such as decreasing viral counts in plasma of patients with AIDS and recognizing recovery of number of CD4.

However, on the other hand, it is apprehensive that macrophage (MΦ) directed virus is remained in the reticuloendothelial tissues[1),2)] and resistant strain to HAART is observed in patients who received HAART in about half year to several years after HAART. Further, since the cost for treatment by HAART is expensive, the treatment is given priority to peoples in the advanced countries, and peoples in the under developing countries can not receive such the treatment due to a disparities in economic power between advanced countries and the under developing countries where there are more than 80% of patients with HIV in the world, and such treatment could not contribute to interrupt international distribution of virus, as a result, multiple combination therapy is required in order to suppress appearance of resistant strains, and patients who are dropped out from the treatment due to abdominal symptom and hematopoietic injury are reported, consequently, limits in the medical and social application for HAART are pointed out.

HIV-1 is a virus which infects to immunocompetent cells such as macrophage and dendritic cell to destroy the immune system. As the results of recent research studies, it is becoming clear that the infection and proliferation of HIV-1 in the macrophage play important roles on the maintenance of infection and the development of pathogenesis of HIV-1[3)], consequently, development of new drugs which inhibit infection and proliferation of HIV-1 in the macrophage is expected.

Although large numbers of infectious experiments on HIV-1 in the macrophage were performed, many studies were carried out using the macrophage cell strains, as the results, the experimental results using such cell strains did not always reflect function of tissue macrophage in vivo. Akagawa et al. succeeded differential induction of two types of the macrophage proceeding proliferation of HIV-1 and the macrophage suppressing proliferation of HIV-1 from the monocytes, further demonstrated that the macrophage suppressing the proliferation could be a model for human alveolar macrophage, as a result, analysis of infection, proliferation and a mechanism for suppression of the proliferation of HIV-1 was made possible in the system similar to the macrophage in vivo[4)-9)].

In addition, macrolides have known that it is effective for treatment of diffuse panbronchiolitis (DPB) and diseases of otorhinology field and a mechanism of action thereof is known, in addition to antibiotic action, to be an induction of antiunflammatory actions[10)]. Especially, as a result of examining accumulation of macrolides in tissues, there is a report indicating several hundreds to a thousand times of accumulation were observed in the macrophage as compared with the peripheral lymphocytes, consequently, action of the macrolides on macrophage is thought to be important.

Based on the above background, we have thought that development of drugs supplementing disadvantages of HAART, suppressing infection and proliferation of HIV-1 in the macrophage and aiming at exclusion of the macrophage directed HIV-1 from the lymphoid reticuloendothelial system, especially development of inexpensive chemotherapeutic agents from the standpoint of therapeutic strategy against AIDS in view of the world wide level is useful for treatment of patients with HIV-1.

We have studied that whether the known macrolides derivatives have actions for inhibiting infection and proliferation of HIV-1 or not, and quite surprisingly found that they have inhibitory actions against infection and proliferation of HIV-1 in the macrophage, and demonstrated that the inhibitory action against the proliferation is exhibited by suppressing expression of tyrosine kinase Hck protein in the macrophage which is essential for viral growth and suppressing activation of P38MAPK, and completed the present invention.

An object of the present invention is to provide use of agent for suppressing infection and proliferation of human immunodeficiency syndrome virus useful for treatment of patients with HIV-1 infection by inexpensive chemotherapeutic agent as well as useful as a supplemental agent in the HAART.

SUMMARY OF THE INVENTION

The present invention relates to use of macrolides derivatives for suppression of infection and proliferation of human immunodeficiency syndrome virus in the macrophage derived from the human monocytes. The macrophage derived from the human monocytes is M type macrophage. The suppression of proliferation of virus is based on the suppressive action of the macrolides on tyrosine kinase Hck protein and suppression for activation of P38MAPK of the macrophage necessary for the viral proliferation. Known macrolides derivatives having such suppressive action against HIV-1 proliferation are all included in the present invention.

Preferable examples of the macrolides derivatives used in the present invention are:

Oxacyclotetradecane-2,10-dione,4[(2,6-dideoxy-3-O-methyl-α-L-ribo-hexopyranosyl)oxy]-14-ethyl-7,12,13-trihydroxy-3,5,7,9,11,13-hexamethyl-6-[[3,4,6-trideoxy-3-(dimethylamino)-β-D-xylo-hexopyranosyl]oxy; 11-(1'-hydroxypropyl)-3-[2,6-dideoxy-3-C-methyl-α-L-ribo-hexopyranosyl]oxy]-5-[(3,4,6-trideoxy- 3-(dimethylamino)-β-D-xylo-hexopyranosyl)oxy]-2,4,6,8,11,14-hexamethyl-10,13,15-tri-oxatricyclo[9.2.1.1.$^{9,6}$]-pentadecane-1-one; 6,15,16-Trioxatricyclo[10.2.1.11,4]hexadecane, erythromycin derivative; 4,13-Dioxabucyclo[8.2.1]tridec-12-en-5-one, 7-[(2,6-dideoxy-3-C-methyl-α-L-ribo-hexopyranosyl)oxy]-

3-(1,2-dihydroxy-1-methylbutyl)-2,6,8,10,12-pentamethyl-9-[[3,4,6-trideoxy-3-(dimethylamino)-β-D-xylo-hyxopyranosyl]oxy]; Oxacyclo-tetradecane-2,10-dione,4-[(2,6-dideoxy-3-O-methyl-α-L-ribo-hexopyranosyl)oxy]-14-ethyl-12,13-dihydroxy-7-methoxy-3,5,7,9,11,13-hexamethyl-6-[[3,4,6-trideoxy-3-(dimethylamino)-β-D-xylo-hyxopyranosyl]oxy]; de(3'-N-methyl)-8,9-anhydro-pseudoerythromycin A 6,9-hemiketal or salt thereof; de(3'-N-methyl)-3'-N-sulfonyl-8,9-anhydro-pseudoerythromycin A 6,9-hemiketal or salt thereof; de(3'-N-methyl)-[3'-N-(3-hydroxy-1-propyl)]-8,9-anhydro-pseudoerythromycin A 6,9-hemiketal or salt thereof; de(3'-N-methyl)-3'-N-(2-acetoxyethyl)-8,9-anhydro-pseudoerythromycin A 6,9-hemiketal or salt thereof; de(3'-N-methyl)-3'-N-cyanomethyl-8,9-anhydro-pseudoerythromycin A 6,9-hemiketal or salt thereof; de(3'-N-methyl)-3'-N-(2-fluoroethyl)-8,9-anhydro-pseudo-erythromycin A 6,9-hemiketal or salt thereof; bis-de(3'-N-methyl)-8,9-anhydro-pseudoerythromycin A 6,9-hemiketal or salt thereof; bis-de(3'-N-methyl )-3'-N-ethyl-8,9-anhydro-pseudo-erythromycin A 6,9-hemiketal or salt thereof; bis-de(3'-N-methyl)-3',3'-N,N-diethyl-8,9-anhydro-pseudoerythromycin A 6,9-hemiketal or salt thereof; bis-de(3'-N-methyl)-3'-N-allyl-8,9-anhydro-pseudoerythromycin A 6,9-hemiketal or salt thereof; bis-de(3'-N-methyl)-3',3'-N,N-diallyl-8,9-anhydro-pseudo-erythromycin A 6,9-hemiketal or salt thereof; bis-de(3'-N-methyl)-3'-N-propargyl-8,9-anhydro-pseudoerythromycin A 6,9-hemiketal or salt thereof; bis-de(3'-N-methyl)-3',3'-N,N-dipropargyl-8,9-anhydro-pseudoerythromycin A 6,9-hemiketal or salt thereof; bis-de(3'-N-methyl)-3'-N-propyl-8,9-anhydro-pseudo-erythromycin A 6,9-hemiketal or salt thereof; bis-de(3'-N-methyl)-3',3'-N,N-dipropyl-8,9-anhydro-pseudoerythromycin A 6,9-hemiketal or salt thereof; bis-de(3'-N-methyl)-3'-N-hexyl-8,9-anhydro-pseudoerythromycin A 6,9-hemiketal or salt thereof; bis-de(3'-N-methyl)-3',3'-N,N-dihexyl-8,9-anhydro-pseudoerythromycin A 6,9-hemiketal or salt thereof; bis-de(3'-N-methyl)-3'-N-benzyl-8,9-anhydro-pseudoerythromycin A 6,9-hemiketal or salt thereof; bis-de(3'-N-methyl)-3',3'-N,N-di-benzyl-8,9-anhydro-pseudoerythromycin A 6,9-hemiketal or salt thereof; bis-de(3'-N-methyl)-3'-N-(2-propyl)-8,9-anhydro-pseudoerythromycin A 6,9-hemiketal or salt thereof; bis-de(3'-N-methyl)-3',3'-N,N-di-(10-bromo-1-decanyl)-8,9-anhydro-pseudoerythromycin A 6,9-hemiketal or salt thereof; bis-de(3'-N-methyl)-3'-N-acetyl-8,9-anhydro-pseudoerythromycin A 6,9-hemiketal or salt thereof; de(3'-dimethylamino)-3'-piperidino-8,9-anhydro-pseudoerythromycin A 6,9-hemiketal or salt thereof; de(3'-dimethylamino)-3'-pyrrolidino-8,9-anhydro-pseudoerythro-mycin A 6,9-hemiketal or salt thereof; de(3'-dimethylamino)-3'-morpholino-8,9-anhydro-pseudoerythromycin A 6,9-hemiketal or salt thereof; de(3'-dimethylamino)-3'-[hexahydro-1(1H)-azepinyl]-8,9-anhydro-pseudoerythromycin A 6,9-hemiketal or salt thereof; de(12-hydroxy)-de[12-(1-hydroxypropyl)]-12-hydroxy-oxime-8,9-anhydro-pseudoerythromycin A 6,9-hemiketal or salt thereof; de[12-(1-hydroxypropyl)]-8,9-anhydro-pseudo-erythro-mycin A 6,9-hemiketal or salt thereof; de(12-hydroxy)-de[12-(1-hydroxypropyl)]-12-amino-8,9-anhydro-pseudoerythromycin A 6,9-hemiketal or salt thereof; de(3'-N-methyl)-de[12-(1-hydroxypropyl)]-8,9-anhydro-pseudoerythromycin A 6,9-hemiketal or salt thereof; de(3-O-cladinosyl)-8,9-anhydro-pseudo-erythromycin A 6,9-hemiketal or salt thereof and de(3-O-cladinosyl)-de(3'-N-methyl)-8,9-anhydro-pseudoerythromycin A 6,9-hemiketal or salt thereof.

In order to understand the present invention, a mechanism of the suppression of proliferation against macrophage directed HIV-1 on macrophage derived from human monocytes is explained.

[I] Experimental Materials and Methods (1-1) Preparation of Macrophage Derived from Human Monocytes and Alveolar Macrophage As previously reported[11], human peripheral-blood mononuclear cells (PMBC) were isolated from buffy coat of the human healthy volunteers using human CD14 antibody micro beads (Miltenyi Biotec, Germany), magnetic cell separation system (MACS) (Miltenyi Biotech, Germany) and lymphoprep (Nycome Inc., Norway), then monocytes were isolated from PMBC by positive selection.

Macrophages derived from monocytes were prepared by culturing the recovered monocytes in the presence of M-CSF (macrophage colony-stimulating factor) ($10^4$ U/ml, provided by Morinaga Milk Co.), granulocytes and granulocyte-macrophage colony-stimulating factor, GM-CSF) (500 U/ml, provided by Japan Scheling Plough Co., Osaka, or purchased from R & S Genzyme-TECHNE Inc.) with RPMI1640 medium added with FCS10% (Nissui Seiyaku Co., Tokyo) for 7–8 days.

The macrophage prepared by differential induction of M-CSF from human monocytes is designated as M type macrophage (M type MΦ or M-MΦ) and the macrophage prepared by differential induction of GM-CSF from human monocytes is designated as GM type macrophage (GM type MΦ or GM-MΦ) Further, alveolar macrophage (alveolar MΦ or A-MΦ) was prepared as follows. Cells in the alveolar lavage liquid obtained from the alveolar lavage of healthy volunteers were recovered, suspended and adhered to plastics, then the non-adhered cells were washed out and the remained adhered cells were designated as the alveolar MΦ.

(1-2) Infection of HIV-1 to Macrophage

Infection of HIV-1 to macrophage was performed as follows. Macrophage directed viral strains, HIV-1$_{JR-FL}$ and HIV-1$_{BAL}$, were infected for 2 hours in contact with M-MΦ, GM-MΦ and A-MΦ (adjusted to $2.5 \times 10^5$/well, Flacon No3043: Becton Dickinson Labware, Inc. U.S.)at low concentration (p24 antigen titer 50 ng/ml, TCID$_{50}$=3000/ml virus to final concentration at 100 pg/ml), and non-adsorbed virus to the macrophage was washed out, and cultured with adding fresh medium. In case of the medium with M-MΦ, M-CSF was added ($10^4$ U/ml), and that of the medium with GM-MΦ, GM-CSF was added (500 U/ml).

Amount of virus used in the contact infection was adjusted to the level of virus in patients at the carrier stage in the present experiments, since viral level of lung tissue in patients at the HIV-1 carrier stage is several-ten pg/ml—several-hundred pg/ml, and the infected viral level in the alveolar MΦ) is several copies in $10^4$ cells[12].

(1-3) Assay of Infected and Proliferated HIV-1

Proliferation of virus was examined with the released viral particles in the culture supernatant after the infection by the sandwich ELISA using two types of anti-p24 antibody (Nu24 and 10B5[13]. The following JAM62 and JAM65 were used as LTR (HIV long terminal repeat)-gap gene primer. The following JAM63 and JAM 64 were used as the internal primer for the nested PCR.

JAM62:

5'-GCTTCAAGTAGTGTGTGCCCGTCTC-3' (SEQ ID NO: 1)

JAM65:
5'-AATCGTTCTAGCTCCCTGCTTGCCC-3' (SEQ ID NO: 2)

JAM63:
5'-GTGTOACTCTGGTAACTAGAGATCC-3' (SEQ ID NO: 3)

JAM64:
5'-CCGCTTAATACTGACGCTCTCGCAC-3' (SEQ ID NO: 4)

(1-4) Assay of Expression of Tyrosine Kinase Hck Protein and Transcription Factor C/EBPβ Protein Expression of tyrosine kinase Hck protein and transcription factor C/EBPβ protein in macrophage was examined after solubilizing the macrophage in SDS-PAGE sample buffer, performing 10% SDS-polyacrylamide electrophoresis, transferring the protein on the gel to immobilon P membrane (Millipore Inc. U.S.) and checking antibodies against these proteins by Western blotting. Antibody to tyrosine kinase Hck protein (N-30) and antibody to C/EBPβ (C-19) were purchased from Santacluse Inc. (U.S.). Western blotting was detected by Amersham ELC Regent (Amersham International plc, Buckinghamshire, UK). Strength of bands was expressed by PSL (photostimulating luminescence) value ($A/mm^2$).

(1-5) Treatment of Macrophage by Antisense Tyrosine Kinase Hck Protein and Transcription Factor C/EBPβ Protein Antisense oligonucleotide probe of Hck protein and C/EBPβ protein (AS), sense oligonucleotide probe corresponding thereto (S) and non-sense oligonucleotide probe without relating to transcription and translation (NS) were used as follows.

Phosphorothioate-modified AS-Hck;
5'-TTCATCGACCCCATCCTGGC-3' (SEQ ID NO: 5)

Phosphorothioate-modified S-Hck;
5'-GCCAGOATGGGTCGATCAA-3' (SEQ ID NO: 6)

Phosphorothioate-modified NS-Hck;
5'-CCATATTTCCCGCTCOCGTG-3' (SEQ ID NO: 7)

Phosphorothioate-moclified AS-C/EBPβ;)
5'-CAGGCGTTGCATGAACGCGG-3' (SEQ ID NO: 8)

Phosphorothioate-modified S-C/EBPβ;
5'-CCGCGTTCATOCAACOCCTG-3' (SEQ ID NO: 9)

Phosphorothicatemodified NS-C/EBPβ;
5'-CCAGAGAGGGCCCGTGTGGA-3' (SEQ ID NO: 10)

These probes were dissolved in the serum free RPMI1640 medium, in which lipofectin (Life Technology Inc., U.S.) was dissolved at 5 μM concentration, at room temperature for 30 minutes, added with RPMI1640 medium, which contains 10% FCS, to the macrophage (final concentration 2 μM) and incubated at 37° C. for 24 hours. Thereafter, cells were washed with the medium, added the RPMI1640 medium containing 10% FCS without oligonucleotide, further cultured for 24 hours, and then infected with HIV-1.

(1-6) Assay of P38MAPK and ERK1/2 Activation

P38MAPK and ERK1/2 activation were determined using P38MAPK antibody, anti-ERK1/2 antibody, anti-tyrosine phosphorylation P38MAPK antibody and anti-tyrosine phosphorylation ERK1/2 antibody (New England Biolabs, Inc. U.S.), and phosphorylation reaction of these molecules was determined by Western blotting.

[2] Result (2-1) Proliferative Response of Macrophage Directed HIV-1 Strain in M-MΦ and GM-MΦ

(2-1-1) Amount of p24 Protein on HIV-1 Infected M-MΦ and GM-MΦin Culture Supernatant M-MΦ and GM-MΦ were infected with HIV-1$_{JR-FL}$ strain and HIV-1$_{BAL}$ strain and incubated for 14 days. Amount of p24 protein in the culture supernatant of the macrophage was detected at constant times. In any of HIV-1 strains, p24 protein was detected in the culture supernatant in M-MΦ [refer to FIGS. 1(A) and (B)].

(2-1-2) Cytopathy in HIV-1 Infected M-MΦ and GM-MΦ

Morphological changes of M-MΦ and GM-MΦ infected with HIV-1$_{JR-FL}$ strain and HIV-1$_{BAL}$ strain were observed in time dependent manner. Formation of cell cluster and cell fusion was observed from the $2^{nd}$ day of the incubation only in virus producing M-MΦ and formation of multinucleatic giant cells were recognized from the culture day 4–7 [refer to FIG. 2(A)]. On the other hand, in GM-MΦ without generation of virus, nomorphological changes were observed [refer to FIG. 2(B)]. These results indicated that the cytopathic effect such as clustering, cell-fusion and MGC formation in the macrophage at the infection of the macrophage directed HIV-1 infection, could be used as an index for determining viral proliferation.

(2-1-3) Analysis of Distribution of Intracellular p24 Protein in HIV-1 Infected M-MΦ and GM-MΦ

M-MΦ and GM-MΦ were infected with HIV-1$_{JR-FL}$ strain and HIV-1$_{BAL}$ strain, and were immunostained by p24 antibody on the infection day 8. In M-MΦ, expression of p24 protein was observed in MGC and its penumbral cells [refer to FIG. 3(A)]. No expression of p24 protein was observed in GM-MΦ [refer to FIG. 3(B)]. These results were estimated that virus production suppressive mechanism in GM-MΦ might be the suppressive mechanism prior to intracellular forming and budding stages of the viral particles.

(2-1-4) Detection of Viral DNA in HIV-1 Infected M-MΦ and GM-MΦ

M-MΦ and GM-MΦ were infected with HIV-1$_{JR-FL}$ strain and HIV-1$_{BAL}$ strain, and were detected viral DNA formation on the infection day 2 by nested PCR using LTR-gag primer. The viral DNA formation was detected in both M-MΦ, in which viral proliferation was recognized, and GM-MΦ, in which no viral DNA formation was recognized [refer to FIGS. 4(A) and (B)]. These results indicated that infiltration of virus into cells and conversion from RNA to DNA occurred even in GM-MΦ without recognizing proliferation of virus, showing that the mechanism of suppression of viral formation in GM-MΦ exists on the point after the viral DNA formation.

(2-1-5) Expression of Tyrosine Kinase Hck Protein and C/EBPβ Protein in M-MΦ and GM-MΦ and Changes of Expression by HIV-1 Infection Since M-MΦ derived from human monocytes strongly induce proliferation of HIV-1 and GM-MΦ inhibits proliferation of virus, we have examined whether differences in infective sensitivity for HIV-1 depend on the differences in the expression of the host protein or not. As a result, expression of tyrosine kinase Hck protein and transcription factor C/EBPβ are demonstrated to be different in both macrophages.

When no virus was infected, tyrosine kinase Hck protein was highly expressed in M-MΦ and less expressed in GM-MΦ (refer to FIG. 5). Although expression of tyrosine kinase Hck protein of M-MΦ was increased in the infection of HIV-1$_{BAL}$ strain on day 2, expression of tyrosine kinase Hck protein of GM-MΦ was inversely decreased (refer to FIG. 5). On the other hand, in the expression of C/EBPβ protein without infection of virus, high molecular type (37 kDa) is only expressed in M-MΦ, but expression of both proteins of high molecular type and low molecular type (23 kDa) in GM-MΦ was recognized (refer to FIG. 6). Although no changes in expression of C/EBPβ protein of M-MΦ was recognized on the day 2 after infection of HIV-1$_{BAL}$ strain, expression of low molecular weight C/EBPβ protein was significantly increased in GM-MΦ, and changes in ratio of the high molecular type and the low molecular type (L/S ratio) were induced (refer to FIG. 6).

(2-1-6) Examination of Infectious Sensitivity of Human Alveolar MΦ HIV-1 and Expression of Tyrosine Kinase Hck Protein and C/EBPβ Protein GM-MΦ induced from human monocytes by GM-CSF was demonstrated to be similar to human alveolar macrophage in morphology, expression of surface marker, productivity of active oxygen and expression of catalase[13),14)]. We have examined that whether HIV-1 infective sensitivity of GM-MΦ derived from human monocytes and human alveolar MΦ was resembled or not.

After infection of HIV-1$_{BAL}$ strain in the alveolar MΦ (A-MΦ), viral DNA was assayed by nested PCR and proliferation of virus was assayed in an amount of p24 protein in the culture supernatant by ELISA. Viral DNA was recognized at any time examined after infection [refer to FIG. 7(B)], but neither detection of p24 protein nor production of virus was recognized by 14 days of incubation [refer to FIG. 7(A)].

As a result of examining expression of alveolar MΦ tyrosine kinase Hck protein and C/EBPβ protein by Western blotting, decrease in expression of tyrosine kinase Hck protein and changes in expression of isoform of C/EBPβ protein, namely expression of the low molecular type C/EBPβ protein (23 kDa) was significantly increased and decrease in L/S ratio was recognized (refer to FIG. 8). These results suggested that a mechanism of suppression of virus production in the human alveolar MΦ and GM-MΦ derived from human monocytes might be highly identical.

(2-1-7) Decrease in Expression of Tyrosine Kinase Hck Protein in Antisense Oligonucleotide Treated M-MΦ Against Tyrosine Kinase Hck Protein and Suppression of Proliferation of HIV-1

M-MΦ was treated with antisense (Hck-AS) against tyrosine kinase Hck protein for 24 hours, and M-MΦ was incubated for further 24 hours and expression of tyrosine kinase Hck protein was examined. As a result, expression of tyrosine kinase Hck protein was significantly decreased as compared with control group (L) (refer to FIG. 9). However, in M-Φ treated with sense probe (Hck-S) or non-related probe (Hck-NS), suppression of expression of tyrosine kinase Hck protein was recognized (refer to FIG. 9).

These M-MΦ pretreated with various oligonucleotides was infected with HIV-1$_{BAL}$ strain and expression of tyrosine kinase Hck protein after day 2 of the infection was checked, decrease in expression of tyrosine kinase Hck protein was recognized only in antisense (Hck-AS) added group, and no suppression of expression of tyrosine kinase Hck protein was recognized in M-MΦ treated with sense probe (Hck-S) or non-related probe (Hck-NS) (refer to FIG. 10). Amount of p24 protein in the culture supernatant on day 4, 7 and 10 after the infection were detected. In M-MΦ treated with antisense (Hck-AS), significant amount of p24 protein was recognized at any time, but in M-MΦ treated with sense probe (Hck-S) and non-related probe (Hck-NS), time-dependent increase in p24 protein was recognized similar to the control group treated only with lipofectin (L) (refer to FIG. 10). These results indicated that expression of tyrosine kinase Hck protein in M-MΦ is essential for proliferation of HIV-1.

(2-1-8) Expression of C/EBPβ and Growth Response of HIV-1 in C/EBPβ Antisense Oligonucleotide Treated GM-MΦ

In GM-MΦ treated with antisense against C/EBPβ(C/EBPβ-AS) for 24 hours and further cultured for 24 hours, and in the GM-Mafter two days of infection with HIV-1$_{BAL}$ strain in the said GM-MΦ, expression of high molecular isoform (37 kDa) was relatively maintained but expression of low molecular isoform (23 kDa) was significantly decreased to recognize increase in L/S ratio (refer to FIG. 11). Further HIV-1 infection to C/EBPβ-AS pretreated GM-MΦ induced proliferation of virus and p24 protein was recognized in the culture supernatant (refer to FIG. 12). The HIV-1 growth promotion effect and changes in expression of C/EBPβ were not recognized in groups added with C/EBPβ-S and C/EBPβ-NS (refer to FIG. 11 and FIG. 12).

From the above experimental results, it was clearly indicated that M-MΦ and GM-MΦ derived from human monocytes have different infective sensitivity against macrophage directed HIV-1, and in M-MΦ, viral proliferation was strongly induced and inversely in GM-MΦ, viral proliferation was suppressed. Further, difference in proliferation pattern in M-MΦ and GM-MΦ was identical with difference in expression of high molecular isoform and low molecular isoform of tyrosine kinase Hck protein and transcription factor C/EPBβ protein in these cells. As the results of specifically regulating expression of isoform of tyrosine kinase Hck protein and C/EPBβ protein using antisense oligonucleotide, viral production in M-MΦ was completely regulated and inversely viral production could be induced in GM-MΦ.

From these results, it was clearly indicated that tyrosine kinase was essential for HIV-1 proliferation in M-MΦ, and low molecular type isoform of C/EBPβ played important role for suppression of HIV-1 proliferation in GM-MΦ. Further, as the results of analysis of the infectious sensitivity of HIV-1 to human alveolar MΦ and expression of tyrosine kinase Hck protein and C/EBPβ, and since mechanisms of HIV-1 growth suppression in human alveolar MΦ and GM-MΦ derived from human monocytes are identical, analysis in GM-MΦ might be highly connected with analysis of alveolar MΦ in vivo. Results of these experiments indicated that analysis of HIV-1 proliferation mechanism in M-MΦ derived from human monocytes was useful as a fundamental experimental system for development of drugs having HIV-1 growth suppressive action.

Based on the above results, preferable examples of macrolides derivatives having suppression of expression of tyrosine kinase Hck protein of M-MΦ derived from human monocytes and suppressive action for activation of P38MAPK activation, which are necessary for viral proliferation, can be mentioned as the following substances, and these substances can easily be commercially available or obtainable according to the method described in the references.

Oxacyclotetradecane-2,10-dione,4[(2,6-dideoxy-3-O-methyl-α-L-ribo-hexopyranosyl)oxy]-14-ethyl-7,12,13-trihydroxy-3,5,7,9,11,13-hexamethyl-6-[[3,4,6-trideoxy-3-

(dimethylamino)-β-D-xylo-hexopyranosyl]oxy (Sigma Inc., U.S.); Hereinafter designates as EM.

11-(1'-hydroxypropyl)-3-[2,6-dideoxy-3-C-methyl-α-L-ribo-hexopyranosyl]oxy]-5-[(3,4,6-trideoxy-3-(dimethylamino)-β-D-xylo-hexopyranosyl)oxy]-2,4,6,8,11,14-hexamethyl-10,13,15-tri-oxatricyclo[9.2.1.1.$^{9.6}$]-pentadecane-1-one (refer to P. Kurath et al. Exoperimentia, 27, 362, 1971); Hereinafter designates as EM201.

6,15,16-Trioxatricyclo[10.2.1.11,4]hexadecane,erythromycin derivarive, or 6,9,12-Anhydroerythromycin A (refer to P. Kurath et al.Exoperimentia, 27, 362, 1971); Hereinafter designates as EM202.

4,13-Dioxabicyclo[8.2.1]tridec-12-en-5-one,7-[(2,6-dideoxy-3-C-methyl-α-L-ribo-hexopyranosyl)oxy]-3-(1,2-dihydroxy-1-methylbutyl)-2,6,8,10,12-pentamethyl-9-[[3,4,6-trideoxy-3-(dimethylamino)-β-D-xylo-hyxopyranosyl]oxy] (refer to JP-A-7-247299); Hereinafter designates as EM703.

Oxacyclotetradecane-2,10-dione,4-[(2,6-dideoxy-3-O-methyl-α-L-ribo-hexopyranosyl)oxy]-14-ethyl-12,13-dihydroxy-7-methoxy-3,5,7,9,11,13-hexamethyl-6-[[3,4,6-trideoxy-3-(dimethylamino)-β-D-xylo-hexopyranosyl]oxy] (refer to S. Morimoto et al. J Antibiotics, 43, 286, 1990 or Product of Apin Chemicals Ltd., UK and product of Wako Pure Chemicals, Inc. Japan); Hereinafter designates as CAM.

Examples of erythromycin derivatives are:
de(3'-N-methyl)-8,9-anhydro-pseudoerythromycin A 6,9-hemiketal or salt thereof; Hereinafter designates as EM703. de(3'-N-methyl)-3'-N-sulfonyl-8,9-anhydro-pseudoerythromycin A 6,9-hemiketal or salt thereof; Hereinafter designates as EM727. de(3'-N-methyl)-[3'-N-(3-hydroxy-1-propyl)]-8,9-anhydro-pseudoerythromycin A 6,9-hemiketal or salt thereof; Hereinafter designates as EM744. de(3'-N-methyl)-3'-N-(2-acetoxyethyl)-8,9-anhydro-pseudoerythromycin A 6,9-hemiketal or salt thereof; Hereinafter designates as EM745. de(3'-N-methyl)-3'-N-cyanomethyl-8,9-anhydro-pseudoerythromycin A 6,9-hemiketal or salt thereof; Hereinafter designates as EM742. de(3'-N-methyl)-3'-N-(2-fluoroethyl)-8,9-anhydro-pseudoerythromycin A 6,9-hemiketal or salt thereof; Hereinafter designates as EM740. bis-de(3'-N-methyl )-8,9-anhydro-pseudoerythromycin A 6,9-hemiketal or salt thereof; Hereinafter designates as EM721. bis-de(3'-N-methyl)-3'-N-ethyl-8,9-anhydro-pseudoerythromycin A6,9-hemiketal or salt thereof; Hereinafter designates as EM722. bis-de(3'-N-methyl)-3',3'-N,N-diethyl-8,9-anhydro-pseudo-erythromycin A 6,9-hemiketal or salt thereof; Hereinafter designates as EM723. bis-de(3'-N-methyl)-3'-N-allyl-8,9-anhydro-pseudoerythromycin A 6,9-hemiketal or salt thereof; Hereinafter designates as EM724. bis-de(3'-N-methyl)-3',3'-N,N-diallyl-8,9-anhydro-pseudoerythromycin A 6,9-hemiketal or salt thereof; Hereinafter designates as EM725. bis-de(3'-N-methyl)-3'-N-propargyl-8,9-anhydro-pseudoerythromycin A 6,9-hemiketal or salt thereof; Hereinafter designates as EM728. bis-de(3'-N-methyl)-3',3'-N,N-di-propargyl-8,9-anhydro-pseudoerythromycin A 6,9-hemiketal or salt thereof; Hereinafter designates as EM729. bis-de(3'-N-methyl)-3'-N-propyl-8,9-anhydro-pseudoerythromycin A 6,9-hemiketal or salt thereof; Hereinafter designates as EM730. bis-de(3'-N-methyl)-3',3'-N,N-dipropyl-8,9-anhydro-pseudo-erythromycin A 6,9-hemiketal or salt thereof; Hereinafter designates as EM731. bis-de(3'-N-methyl)-3'-N-hexyl-8,9-anhydro-pseudoerythromycin A 6,9-hemiketal or salt thereof; Hereinafter designates as EM738. bis-de(3'-N-methyl )-3',3'-N,N-di-hexyl-8,9-anhydro-pseudoerythromycin A 6,9-hemiketal or salt thereof; Hereinafter designates as EM739. bis-de(3'-N-methyl)-3'-N-benzyl-8,9-anhydro-pseudo-erythromycin A 6,9-hemiketal or salt thereof; Hereinafter designates as EM732. bis-de(3'-N-methyl)-3',3'-N,N-dibenzyl-8,9-anhydro-pseudo-erythromycin A 6,9-hemiketal or salt thereof; Hereinafter designates as EM733. bis-de(3'-N-methyl)-3'-N-(2-propyl)-8,9-anhydro-pseudoerythromycin A 6,9-hemiketal or salt thereof; Hereinafter designates as EM736. bis-de(3'-N-methyl)-3',3'-N,N-di-(10-bromo-1-decanyl)-8,9-anhydro-pseudoerythromycin A 6,9-hemiketal or salt thereof; Hereinafter designates as EM749. bis-de(3'-N-methyl)-3'-N-acetyl-8,9-anhydro-pseudoerythromycin A 6,9-hemiketal or salt thereof; Hereinafter designates as EM726. de(3'-dimethylamino)-3'-piperidino-8,9-anhydro-pseudo-erythromycin A 6,9-hemiketal or salt thereof; Hereinafter designates as EM734. de(3'-dimethylcumino)-3'-pyrrolidino-8,9-anhydro-pseudoerythromycin A 6,9-hemiketal or salt thereof; Hereinafter designates as EM735. de(3'-dimethylamino)-3'-morpholino-8,9-anhydro-pseudoerythromycin A 6,9-hemiketal or salt thereof; Hereinafter designates as EM747. de(3'-dimethyl-amino)-3'-[hexahydro-1(1H)-azepinyl]-8,9-anhydro-pseudo-erythromycin A 6,9-hemiketal or salt thereof; Hereinafter designates as EM748. de(12-hydroxy)-de[12-(1-hydroxypropyl)]-12-hydroxyoxime-8,9-anhydro-pseudoerythromycin A 6,9-hemiketal or salt thereof; Hereinafter designates as EM743. de[12 -(hydroxypropyl)]-8,9-anhydro-pseudoerythromycin A 6,9-hemiketal or salt thereof; Hereinafter designates as EM746. de(12-hydroxy)-de[12-(1-hydroxypropyl)]-12-amino-8,9-anhydro-pseudo-erythromycin A 6,9-hemiketal or salt thereof; Hereinafter designates as EM750. de(3'-N-methyl)-de[12-(1-hydroxypropyl)]-8,9-anhydro-pseudoerythromycin A 6,9-hemiketal or salt thereof; Hereinafter designates as EM751. de(3-O-cladinosyl)-8,9-anhydro -pseudoerythromycin A 6,9-hemiketal or salt thereof; Hereinafter designates as EM737 and de(3-O-cladinosyl)-de(3'-N-methyl)-8,9-anhydro-pseudoerythromycin A 6,9-hemiketal or salt thereof; Hereinafter designates as EM754.

The various erythromycin derivatives hereinabove were found by the present inventors, Satoshi Omura et al., and were applied as the international patent application, the International Publication WO 02/14338A1, including pseudoerythromycin, which is expected to be the novel antiinflammatory agent. In the specification of WO 02/14338A1, synthetic methods and chemical structures of the erythromycin derivatives are described in detail, and outlines of the synthetic methods of each erythromycin derivative are explained hereinbelow.

Synthesis of EM701

Glacial acetic acid solution of erythromycin (12.4 g) was stirred at room temperature for 2 hours, added slowly aqueous sodium hydrogen carbonate and neutralized. The reaction mixture was extracted with chloroform, dehydrated the organic layer with mirabilite, filtered off the mirabilite and removed the solvent by distillation to obtain crude substance. The crude substance was purified with silica gel column chromatography (chloroform:methanol:aqueous ammonia=10:0.5:0.01→10:1:0.05) to obtain EM201 (7.7 g). Subsequently, potassium carbonate (1.4 g) was added to the methanol solution of EM201 (7.6 g) and refluxed for 2 hours. After distilled off the solvent, the residue was dissolved in aqueous sodium hydrogen carbonate and extracted with chloroform. The mixture was dehydrated with mirabilite, filtered and removed the mirabilite, then the obtained crude substance was purified by silicagel column chromatography (chloroform:methanol:aqueous ammonia=10:0.5:0.01→10:1:0.05) to obtain EM701 (5.9 g, white powder).

Synthesis of de(3'-N-methyl)-8,9-anhydro-pseudoerythromycin A 6,9-hemiketal (EM703)

Sodium acetate (3.9 g) and iodine (2.5 g) were added in this order to methanol (52.0 mL)-water (13.0 mL) solution of EM701 (6.9 g) at room temperature, and stirred at 50° C. for 3 hours. During the stirring, 1N aqueous solution of sodium hydroxide was added to maintain at pH 8–9 continuously. After confirming the completion of the reaction by TLC, the reaction mixture was diluted with aqueous ammonia (7.5 mL)-water (200 mL) and extracted with dichloromethane. After dehydrating the organic layer with mirabilite, the mirabilite was removed by filtration and distilled off the solvent to obtain crude substance. The crude substance was purified by silica gel column chromatography (chloroform:methanol:aqueous ammonia=10:0.5:0.01→10:1:0.05) to obtain EM703 (4.8 g, white powder).

Synthesis of bis-de(3'-N-methyl)-8,9-anhydro-pseudoerythromycin A 6,9-hemiketal (EM721)

Sodium (4.5 g) was added in methanol (15 mL) to prepare methanol solution of sodium methoxide, and EM703 (195.4 mg) and iodine (353.6 mg) were added in this order at 0° C. and stirred for 3 hours. After confirming completion of the reaction by TLC, sodium thiosulfate (0.8 g), aqueous ammonia (0.5 mL) and water (80 mL) were added and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=10:0.5:0.01→10:1:0.05) to obtain EM721 (166.3 mg, white powder).

Synthesis of bis-de(3'-N-methyl)-3'-N-ethyl-8,9-anhydro-pseudo-erythromycin A 6,9-hemiketal (EM722)

N,N-diisopropylethylamine (26.6 µL) and ethyl iodide (12.2 µL) were added to dimethylformamide (1.0 mL) solution of EM721 (21.0 mg) and stirred at room temperature for 4 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=10:0.5:0.01→10:1:0.05) to obtain EM722 (7.0 mg, white powder).

Synthesis of bis-de(3'-N-methyl)-3',3'-N,N-diethyl-8,9-anhydro-pseudoerythromycin A 6,9-hemiketal (EM723)

N,N-diisopropylethylamine (26.6 µL) and ethyl iodide (12.2 µL) were added to dimethylformamide (1.0 mL) solution of EM721 (21.0 mg) and stirred at room temperature for 4 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=10:0.5:0.01→10:1:0.05) to obtain EM723 (10.3 mg, white powder).

Synthesis of bis-de(3'-N-methyl)-3'-N-allyl-8,9-anhydro-pseudo-erythromycin A 6,9-hemiketal (EM724)

Allyl bromide (148.3 µL) was added to dichloromethane (5.7 ml)solution of EM721 (117.8 mg) and N,N-diisopropylethylamine (298.6 µl) at 0° C. and stirred at room temperature for 2 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=10:0.5:0.01→10:1:0.05) to obtain EM724 (21.9 mg, white powder).

Synthesis of bis-de(3'-N-methyl)-3',3'-N,N-diallyl-8,9-anhydro-pseudoerythromycin A 6,9-hemiketal (EM725)

Allyl bromide (148.3 µL) was added to dichloromethane (5.7 mL) solution of EM721 (117.8 mg) and N,N-diisopropylethylamine (298.6 µL) at 0° C. and stirred at room temperature for 2 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=10:0.5:0.01→10:1:0.05) to obtain EM 725 (64.3 mg, white powder).

Synthesis of bis-de(3'-N-methyl)-3'-N-acetyl-8,9-anhydro-pseudo-erythromycin A 6,9-hemiketal (EM726)

Acetic anhydride (8.4 µL) was added to dichloromethane (1.6 mL) solution of EM721 (34.8 mg) at 0° C., stirred for 10 minutes and further stirred at room temperature for 30 minutes. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol=100:1→20:1) to obtain EM726 (33.4 mg, white powder).

Synthesis of de(3'-N-methyl)-3'-N-sulfonyl-8,9-anhydro-pseudo-erythromycin A 6,9-hemiketal (EM727)

Methanesulfonyl chloride (9.3 µL) was added to dichloromethane (4.2 ml) solution of EM703 (87.6 mg) at 0° C. and stirred for 3 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol=100:1→20:1) to obtain EM727 (37.2 mg, white powder).

Synthesis of bis-de(3'-N-methyl)-3'-N-propargyl-8,9-anhydro-pseudoerythromycin A 6,9-hemiketal (EM728)

3-bromopropine (137.8 µL) was added to dichloromethane (5.2 mL) solution of EM721 (106.3 mg) and N,N-diisopropylethylamine (269.3 µL)and stirred at room temperature for 24 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=10:0.5:0.01→10:1:0.05) to obtain EM728 (41.3 mg, white powder).

Synthesis of bis-de(3'-N-methyl)-3',3'-N,N-dipropargyl-8,9-anhydro-pseudoerythromycin A 6,9-hemiketal (EM729)

3-bromopropine (137.8 µL) was added to dichloromethane (5.2 mL) solution of EM721 (106.3 mg) and N,N-diisopropylethylamine (269.3 μL) and stirred at room temperature for 24 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=10:0.5:0.01→10:1:0.05) to obtain EM729 (27.9 mg, white powder).

Synthesis of bis-de(3'-N-methyl)-3'-N-propyl-8,9-anhydro-pseudo-erythromycin A 6,9-hemiketal (EM730)

N,N-diisopropylethylamine (59.6 μL) and 1-iodopropine (33.3 μL) were added in this order to acetonitrile (2.3 mL) solution of EM721 (23.5 mg) and refluxed at 80° C. for 20 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=15:1:0.1) to obtain EM730 (5.7 mg, white powder).

Synthesis of bis-de(3'-N-methyl)-3',3'-N,N-dipropyl-8,9-anhydro-pseudoerythromycin A 6,9-hemiketal (EM731)

N,N-diisopropylethylamine (59.6 μL) and 1-iodopropine (33.3 μL) were added in this order to acetonitrile (2.3 mL) solution of EM721 (23.5 mg) and refluxed at 80° C. for 20 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=15:1:0.1) to obtain EM731 (12.0 mg, white powder).

Synthesis of bis-de(3'-N-methyl)-3'-N-benzyl-8,9-anhydro-pseudo-erythromycin A 6,9-hemiketal (EM732)

Benzyl chloride (297.3 μL) was added to dichloromethane (4.3 mL) solution of EM721 (88.8 mg) and N,N-diisopropylethylamine (450.1 μL) at room temperature and stirred for 96 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=15:1:0.1) to obtain EM732 (49.9 mg, white powder).

Synthesis of bis-de(3'-N-methyl)-3',3'-N,N-dibenzyl-8,9-anhydro-pseudoerythromycin A 6,9-hemiketal (EM733)

N,N-diisopropylethylamine (135.99 μL) and benzylchloride (89.7 μL) were added in this order to acetonitrile (1.3 mL) solution of EM721 (26.8 mg) and refluxed at 80° C. for 60 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=20:1:0.1 ) to obtain EM733 (19.6 mg, white powder).

Synthesis of de(3'-dimethylamino)-3'-piperidino-8,9-anhydro-pseudoerythromycin A 6,9-hemiketal (EM734)

N,N-diisopropylethylamine (42.5 μL) and 1,5-dibromopentane (33.2 μL) were added in this order to acetonitrile (4.9 mL) solution of EM721 (16.8 mg) and refluxed at 80° C. for 24 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=15:1:0.1) to obtain EM734 (13.3 mg, white powder).

Synthesis of de(3'-dimethylamino)-3'-pyrrolidino-8,9-anhydro-pseudoerythromycin A 6,9-hemiketal (EM735)

N,N-diisopropylethylamine (40.2 μL) and 1,4-dibromobutane (27.6 μL) were added in this order to acetonitrile (4.6 mL) solution of EM721 (15.9 mg) and refluxed at 80° C. for 24 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=10:1:0.1) to obtain EM735 (11.9 mg, white powder).

Synthesis of bis-de(3'-N-methyl)-3'-N-(2-propyl)-8,9-anhydro-pseudoerythromycin A 6,9-hemiketal (EM736)

N,N-diisopropylethylamine (459.2 μL) and 2-bromopropane (247.5 μL) were added in this order to acetonitrile (4.4 mL) solution of EM721 (90.6 mg) and stirred at 80° C. for 72 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=10:1:0.1) to obtain EM736 (25.3 mg, white powder). The raw material EM721 was recovered 47.1 mg.

Synthesis of de(3-O-cladinosyl)-8,9-anhydro-pseudoerythromycin A 6,9-hemiketal (EM737)

p-toluenesulfonic acid monohydrate (80.3 mg) was added to dimethylformamide (5.6 mL) solution of EM701 (201.6 mg) and stirred at 5° C. for 8 hours. After confirming the completion of the reaction by TLC, the reaction mixture was diluted with water, adjusted to pH 8.0 by adding saturated aqueous sodium hydrogen carbonate and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=20:1:0.1) to obtain EM737 (84.7 mg, white powder).

Synthesis of bis-de(3'-N-methyl)-3'-N-hexyl-8,9-anhydro-pseudo-erythromycin A 6,9-hemiketal (EM738)

N,N-diisopropylethylamine (408.5 μL) and 1-bromohexane (328.7 μL) were added in this order to acetonitrile (3.9 mL) solution of EM721 (80.6 mg) and stirred at 60° C. for 24 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=15:1:0.1) to obtain EM738 (33.7 mg, white powder). The raw material EM721 was recovered 24.6 mg.

Synthesis of bis-de(3'-N-methyl)-3',3'-N,N-dihexyl-8,9-anhydro-pseudoerythromycin A 6,9-hemiketal (EM739)

N,N-diisopropylethylamine (116.0 µL) and 1-bromohexane (93.6 µL) were added in this order to acetonitrile (1.1 mL) solution of EM721 (22.9 mg) and stirred at 60° C. for 72 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=20:1:0.1) to obtain EM739 (20.1 mg, white powder).

Synthesis of de(3'-N-methyl)-3'-N-(2-fluoroethyl)-8,9-anhydro-pseudoerythromycin A 6,9-hemiketal (EM740)

N,N-diisopropylethylamine (347.7 µL) and 1-bromo-2-fluoro-ethane(148.6 µL) were added to dimethylformamide (3.3 mL) solution of EM703 (70.0 mg) at room temperature and stirred for 48 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=20:1:0.1) to obtain EM740 (36.0 mg, white powder). The raw material EM703was recovered 25.5 mg.

Synthesis of de(3'-N-methyl)-3'-N-cyanomethyl-8,9-anhydro-pseudoerythromycin A 6,9-hemiketal (EM742)

N,N-diisopropylethylamine (320.9 µL) and bromoacetonitrile (128.3 µL) were added to dimethylformamide (3.1 mL) solution of EM703 (64.6 mg) at room temperature and stirred for 4 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=20:1:0.1) to obtain EM742 (53.1 mg, white powder).

Synthesis of de(12-hydroxy)-de[12-(1-hydroxy-propyl)]-12-oxo-8,9-anhydro-pseudoerythromycin A 6,9-hemiketal (EM705)

Lead tetraacetate (508.0 mg) was added to dichloromethane (24.0 mL) solution of EM701 (508.0 mg) and stirred at room temperature for 40 minutes. After confirming the completion of the reaction by TLC, the reaction mixture was diluted with saturated brine-aqueous saturated sodium hydrogen carbonate (1:1, v/v) and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueousammonia=10:0.5:0.01) to obtain EM705 (282.7 mg, white powder).

Synthesis of de(12-hydroxy)-de[12-(1-hydroxypropyl)]-12-hydroxy-oxime-8,9-anhydro-pseudoerythromycin A 6,9-hemiketal (EM743)

Pyridine (0.9 mL) was slowly added at 0° C. to ethanol (0.9 mL) solution of EM705 (116.5 mg) and hydroxylamine hydrochloride (32.0 mg) and stirred for 3 hours. After confirming the completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=10:0.5:0.01→10:1:0.05) to obtain EM743(114.5 mg, white powder).

Synthesis of de(3'-N-methyl)-[3'-N-(3-hydroxy-1-propyl)-8,9-anhydro-pseudoerythromycin A 6,9-hemiketal (EM744)

N,N-diisopropylethylamine (338.3 µL) and 3-bromo-1-propanol (175.6 µL) were added to dimethylformamide (3.3 mL) solution of EM703(68.1 mg) at room temperature and stirred for 48 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=15:1:0.1) to obtain EM744 (27.7 mg, white powder). The raw material EM703 was recovered 22.5 mg.

Synthesis of de(3'-N-methyl)-3'-N-(acetoxyethyl)-8,9-anhydro-pseudoerythromycin A 6,9-hemiketal (EM745)

N,N-diisopropylethylamine (106.8 µL) and 2-bromoethyl acetate (67.6 µL) were added to dimethylformamide (1.0 mL) solution of EM703 (21.5 mg) at room temperature and stirred for 48 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=20:1:0.1) to obtain EM745 (6.0 mg, white powder).

Synthesis of de[12-(1-hydroxypropyl)]-8,9-anhydro-pseudo-erythromycin A 6,9-hemiketal (EM746)

Sodium borohydride (21.8 mg) was added to methanol (2.9 mL) solution of EM705 (37.7 mg) at −78° C. and stirred for 30 minutes. Temperature of the reaction mixture was increased to 0° C. and further stirred for 30 minutes. After confirming completion of the reaction by TLC, the reaction was terminated by adding acetone (0.5 ml). The reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueousammonia=15:1:0.1) to obtain EM746 (35.8 mg, white powder).

Synthesis of de(3'-dimethylamino)-3'-morpholino-8,9-anhydro-pseudoerythromycin A 6,9-hemiketal (EM747)

N,N-diisopropylethylamine (45.8 µL) and bis(2-bromoethyl) ether (33.1 µL) were added in this order to acetonitrile (2.6 mL) solution of EM721 (18.1 mg) and stirred at 80° C. for 24 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=20:1:0.1) to obtain EM747 (12.0 mg, white powder).

Synthesis of de(3'-dimethylamino)-3'-[hexahydro-1(1H)-azepinyl]-8,9-anhydro-pseudoerythromycin A 6,9-hemiketal (EM748)

N,N-diisopropylethylamine (49.5 µL) and 1,6-dibromohexane (43.6 µL) were added in this order to acetonitrile (2.8 ml) solution of EM721 (19.5 mg) and stirred at 80° C. for 24 hours. After confirming completion of the reaction by TLC, the reaction mixture was diluted with water and extracted with dichloromethane. The organic layer was dehydrated by adding mirabilite, filtered to remove the mirabilite, and removed the solvent lo obtain crude substance. The crude substance was purified by silica gel column chromatography (chloroform:methanol:aqueous ammonia=20:1:0.1) to obtain EM748 (11.7 mg, white powder).

Synthesis of bis-de(3'-N-methyl)-3',3'-N,N-di-(10-bromo-1-decanyl)-8,9-anhydro-pseudoerythromycin A 6,9-hemiketal (EM749)

N,N-diisopropylethylamine (45.6 µL) and 1,10-dibromodecane (58.9 µL) were added in this order to acetonitrile (2.6 mL) solution of EM721 (18.0 mg) and refluxed at 80° C. for 36 hours. After confirming completion of the reaction by TLC, the reaction mixture was diluted with water and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=20:1:0.1) to obtain EM749 (14.9 mg, white powder).

Synthesis of de(12-hydroxy)-de[12-(1-hydroxypropyl)]-12-amino-8,9-anhydro-pseudoerythromycin A 6,9-hemiketal (EM750)

Molybdenum oxide (IV) (10.0 mg) and sodium borohydride (10.5 mg) were added to ethanol (2.3 mL) solution of EM743 (15.5 mg) at 0° C. and stirred for 4 hours. After confirming the completion of the reaction by TLC, the reaction was terminated by adding acetone (0.5 mL), and the reaction mixture was diluted with saturated brine-aqueous saturated sodium hydrogen carbonate (1:1, v/v) and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=10:1:0.1) to obtain EM750 (13.4 mg, white powder).

Synthesis of de(3'-N-methyl)-de(12-hydroxy)-de-[12-(1-hydroxy-propyl)]-12-oxo-8,9-anhydro-pseudoerythromycin A 6,9-hemiketal (EM706)

Lead tetraacetate (508.0 mg) was added to dichloromethane (24.0 mL) solution of EM701 (508.0 mg) and stirred at room temperature for 40 minutes. After confirming the completion of the reaction by TLC, the reaction mixture was diluted with saturated brine-aqueous saturated sodium hydrogen carbonate (1:1, v/v) and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueousammonia=10:0.5:0.01) to obtain EM706 (71.6 mg, white powder).

Synthesis of de(3'-N-methyl)-de[12-(1-hydroxypropyl)]-8,9-anhydro-pseudoerythromycin A 6,9-hemiketal (EM751)

Sodium borohydride (22.9 mg) were added to methanol (3.0 mL) solution of EM706 (38.8 mg) at 0° C. and stirred for 1 hour. After confirming the completion of the reaction by TLC, the reaction was terminated by adding acetone (0.5 mL), and the reaction mixture was diluted with saturated brine-aqueous saturated sodium hydrogen carbonate (1:1, v/v) and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=15:1:0.1) to obtain EM751 (31.4 mg, white powder).

Synthesis of de(3-O-cladinosyl)-de(3'-N-methyl)-8,9-anhydro-pseudoerythromycin A 6,9-hemiketal (EM754)

p-toluenesulfonic acid monohydrate (53.9 mg) was added to dimethylformamide (3.8 mL) solution of EM703 (132.4 mg) and stirred at 50° C. for 6 hours. After confirming the completion of the reaction by TLC, the reaction mixture was diluted with water, adjusted to pH 8.0 by adding saturated aqueous sodium hydrogen carbonate and extracted with dichloromethane. The organic layer was dehydrated by adding mirabilite, filtered to remove the mirabilite, and removed the solvent to obtain crude substance. The crude substance was purified by silica gel column chromatography (chloroform:methanol:aqueous ammonia=15:1:0.1) to obtain EM754 (50.2 mg, white powder).

DETAILED DESCRIPTION OF PREFERRED EMBODIMENTS

The present invention will be explained concretely with the following examples, but is not limited within these examples.

In order to show growth suppression effect of the present invention, among macrolide derivatives, EM, EM201, EM202, EM703, CAM, EM722, EM730, EM732, EM736, EM734, EM735, EM747, EM748, EM743, EM746, EM750 or EM751 was dissolved in DMSO with each 100 mM concentration, and used in dilution with the medium thereafter. A control group was M-MΦ treated only with DMSO used for dissolving macrolide derivatives.

M-MΦ and GM-M Φ were subjected to contact infection with HIV-1$_{BAL}$ strain for 2 hours, added 30 μM of EM, EM201, EM202, EM703, CAM, EM722, EM730, EM732, EM736, EM734, EM735, EM747, EM748, EM743, EM746, EM750 or EM751, incubated for 14 days and amount of p24 protein in the cultured supernatant was assayed in the time-dependent manner.

EXAMPLE 1

Effect of EM, EM201, EM202, EM703 or CAM on proliferation of HIV-1 in M-MΦ and GM-MΦ.

Figure 1:
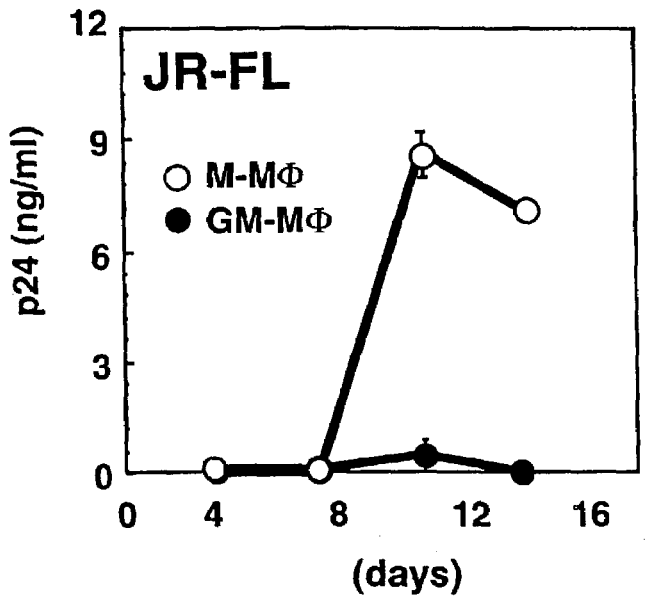
FIG. 1(A) shows amount of p24 protein in the culture supernatant in HIV-1$_{JR-FL}$ strain infected M-MΦ and GM-MΦ, and (B) shows amount of p24 protein in the culture supernatant in HIV-1$_{BAL}$ strain infected M-MΦ and GM-MΦ.
Figure 1:
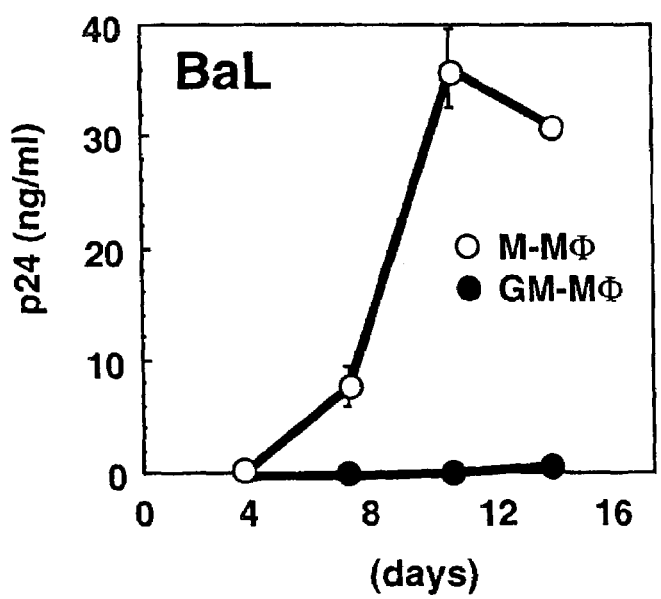
Figure 2:
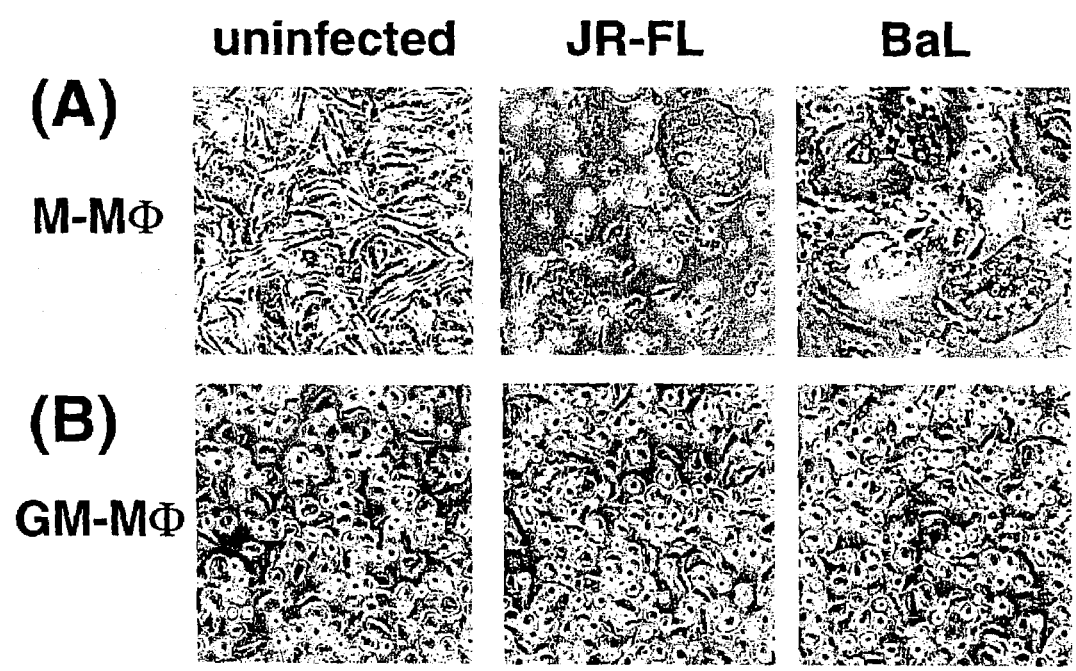
FIG. 2(A) shows cytopathy of HIV-1$_{JR-FL}$ strain and HIV-1$_{BAL}$ strain infected M-MΦ, and (B) shows cytopathy of HIV-1$_{JR-FL}$ strain and HIV-1$_{BAL}$ strain infected GM-MΦ.
Figure 3:
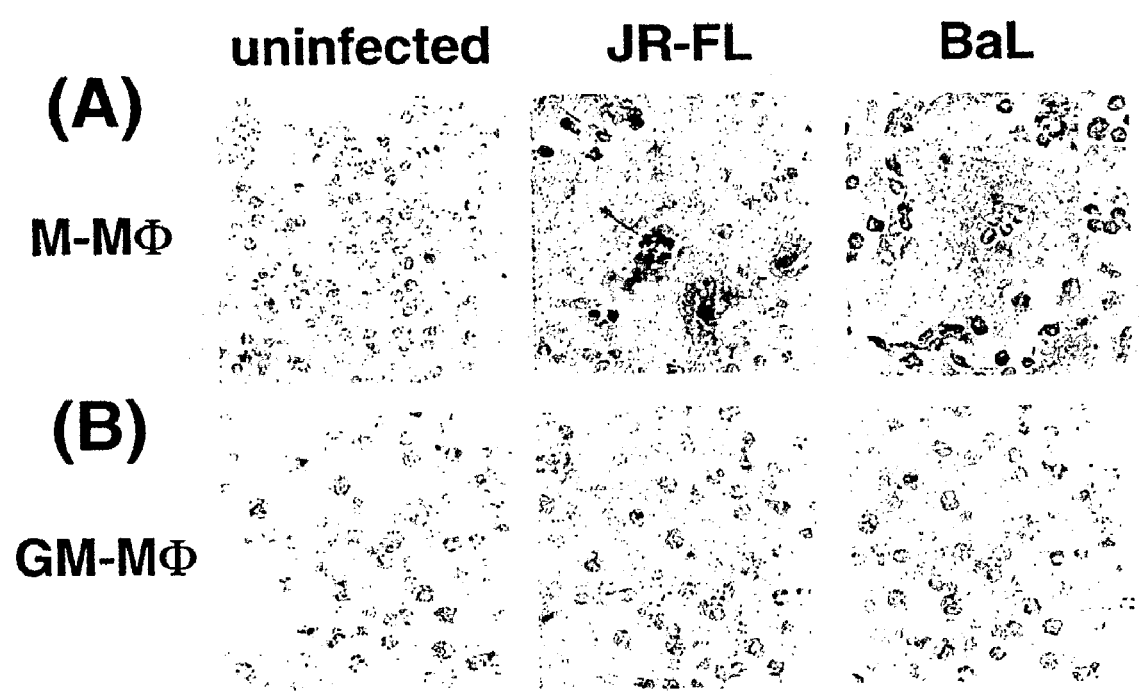
FIG. 3(A) shows intracellular distribution of p24 protein in HIV-1$_{JR-FL}$ strain and HIV-1$_{BAL}$ strain infected M-MΦ, and (B) shows intracellular distribution of p24 protein in HIV-1$_{JR-FL}$ strain and HIV-1$_{BAL}$ strain infected GM-MΦ.
Figure 4:
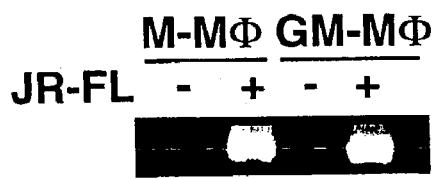
FIG. 4(A) shows detection of viral DNA in HIV-1$_{JR-FL}$ strain infected M-MΦ and GM-MΦ, and (B) shows detection of viral DNA in HIV-1$_{BAL}$ strain infected M-MΦ and GM-MΦ.
Figure 4:
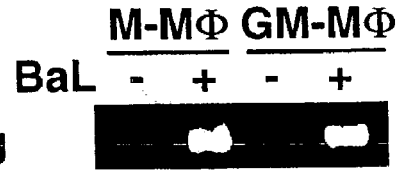
Figure 5:
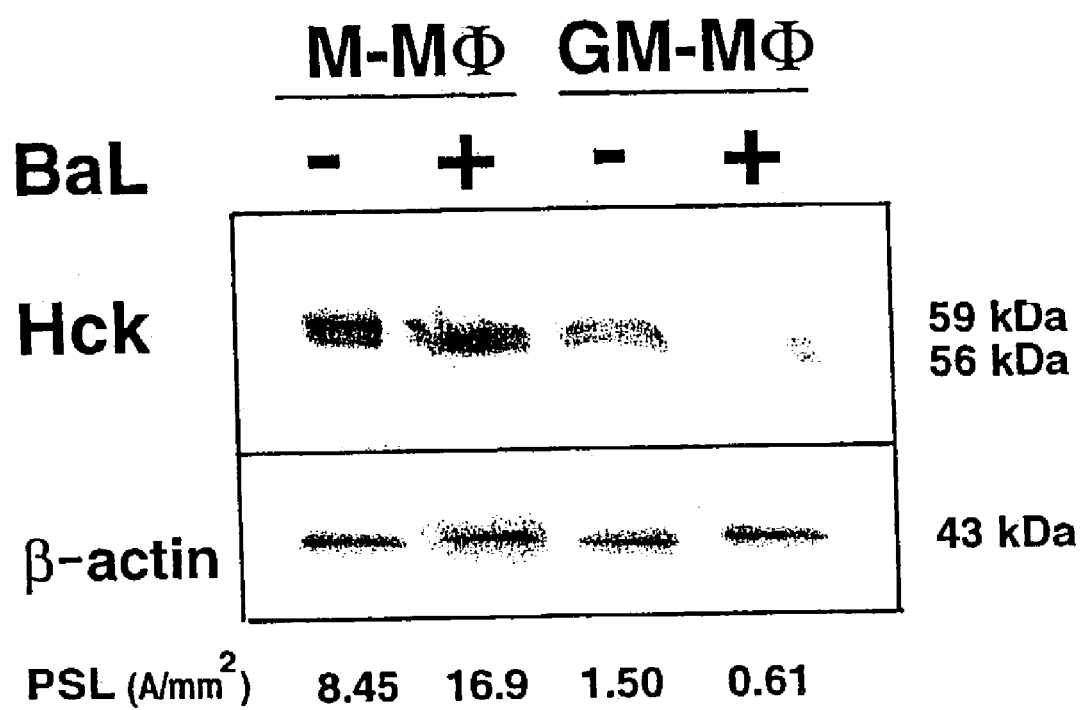
FIG. 5 shows changes of an expression of tyrosine kinase Hck protein in M-MΦ and GM-MΦ and the expression by HIV-1$_{BAL}$ strain infection.
Figure 6:
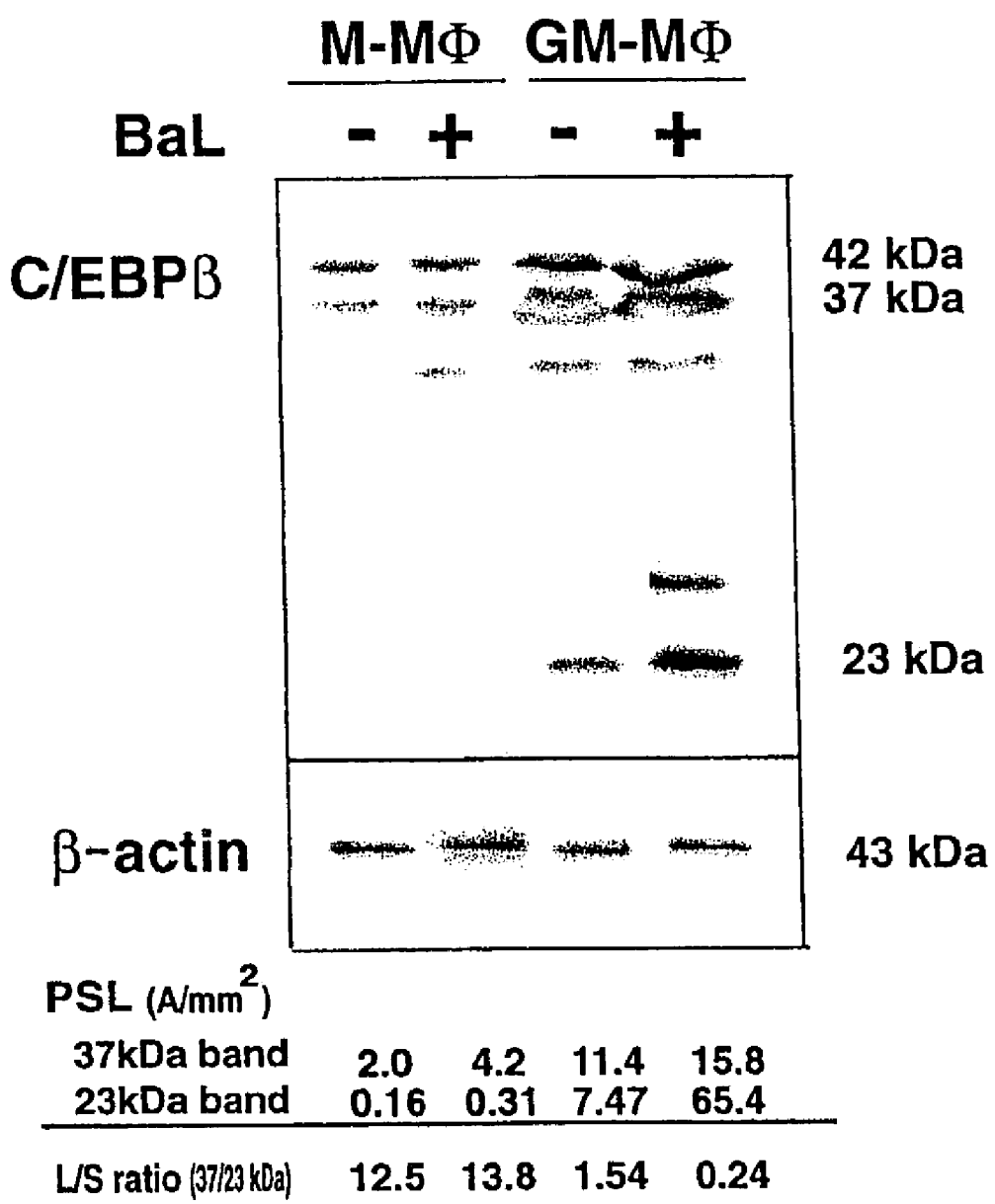
FIG. 6 shows changes of an expression of C/EBPβ protein in M-MΦ and GM-MΦ and the expression by HIV-1$_{BAL}$ strain infected M-MΦ and GM-MΦ.
Figure 7:
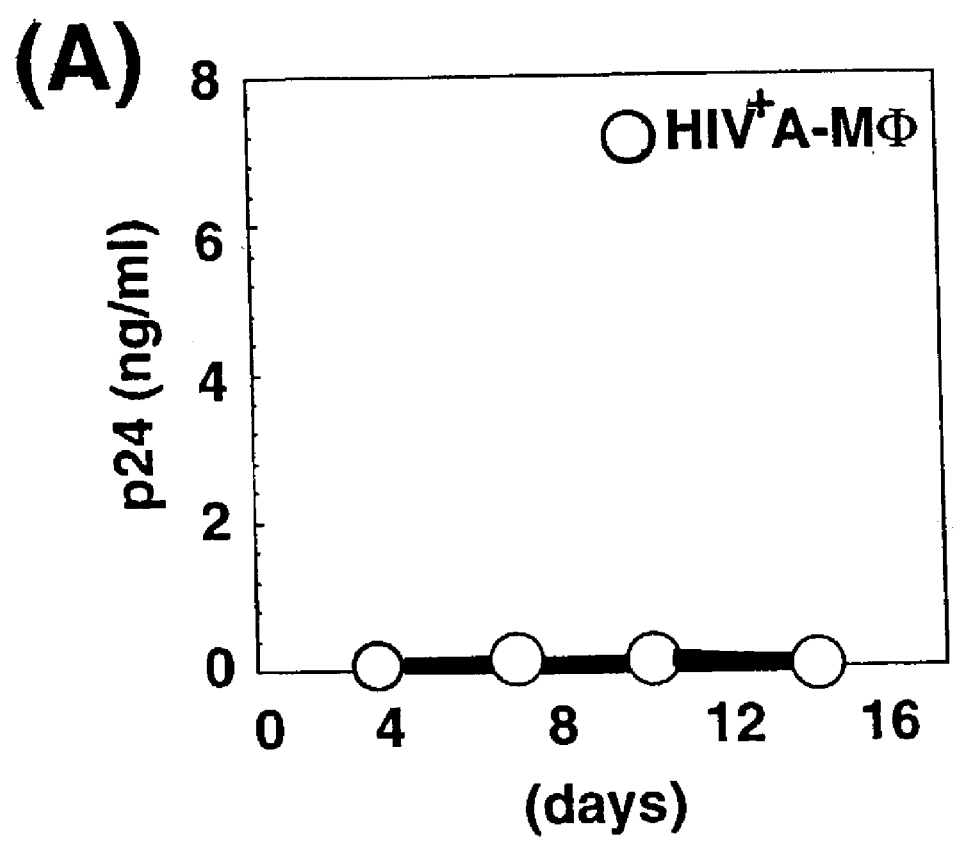
FIG. 7(A) shows HIV-1 growth response by detection of p24 protein in the culture supernatant after infection of HIV-1$_{BAL}$ strain in human alveolar MΦ (A-MΦ) and (B) shows detection of viral DNA.
Figure 7:
Figure 8:
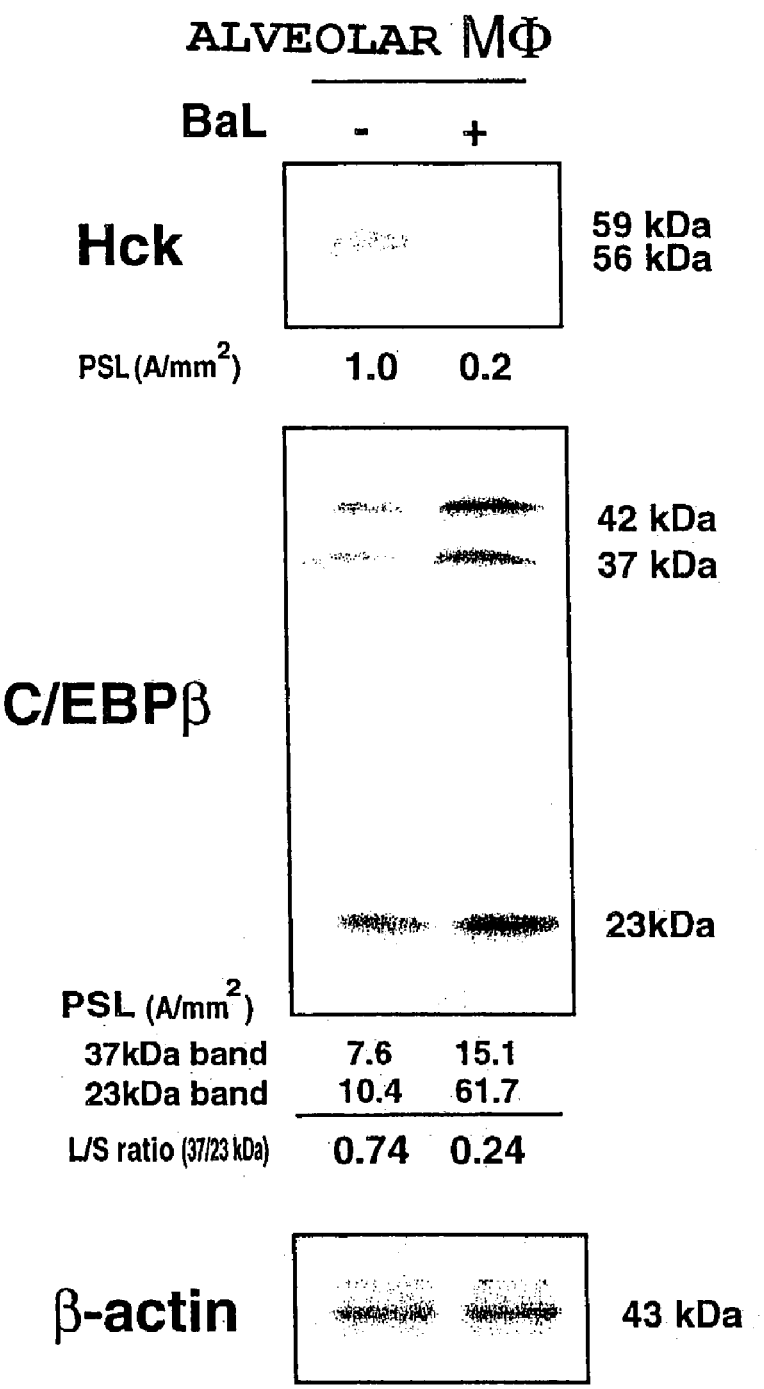
FIG. 8 shows changes of an expression of tyrosine kinase Hck protein and C/EBPβ protein in alveolar MΦ and the expression by HIV-1$_{BAL}$ strain infection.
Figure 9:
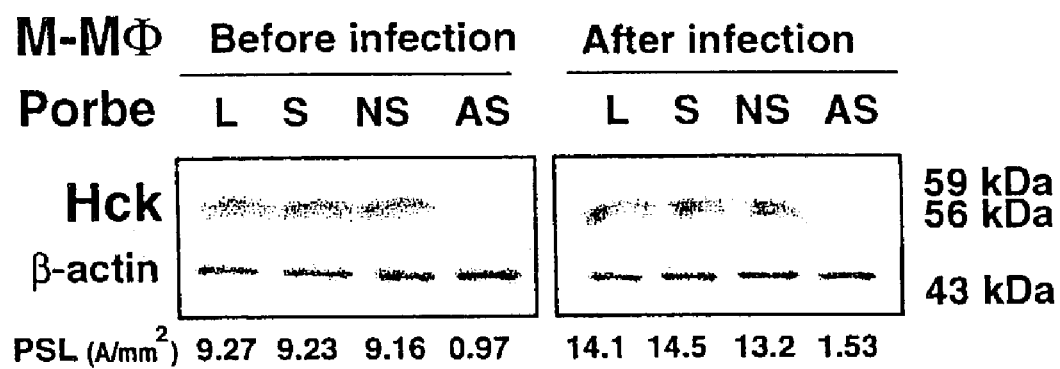
FIG. 9 shown the expression of Hck protein in M-MΦ treated by antisense oligonucleotide for tyrosine kinase Hck protein before and after infection of HIV-1$_{BAL}$ strain.
Figure 10:
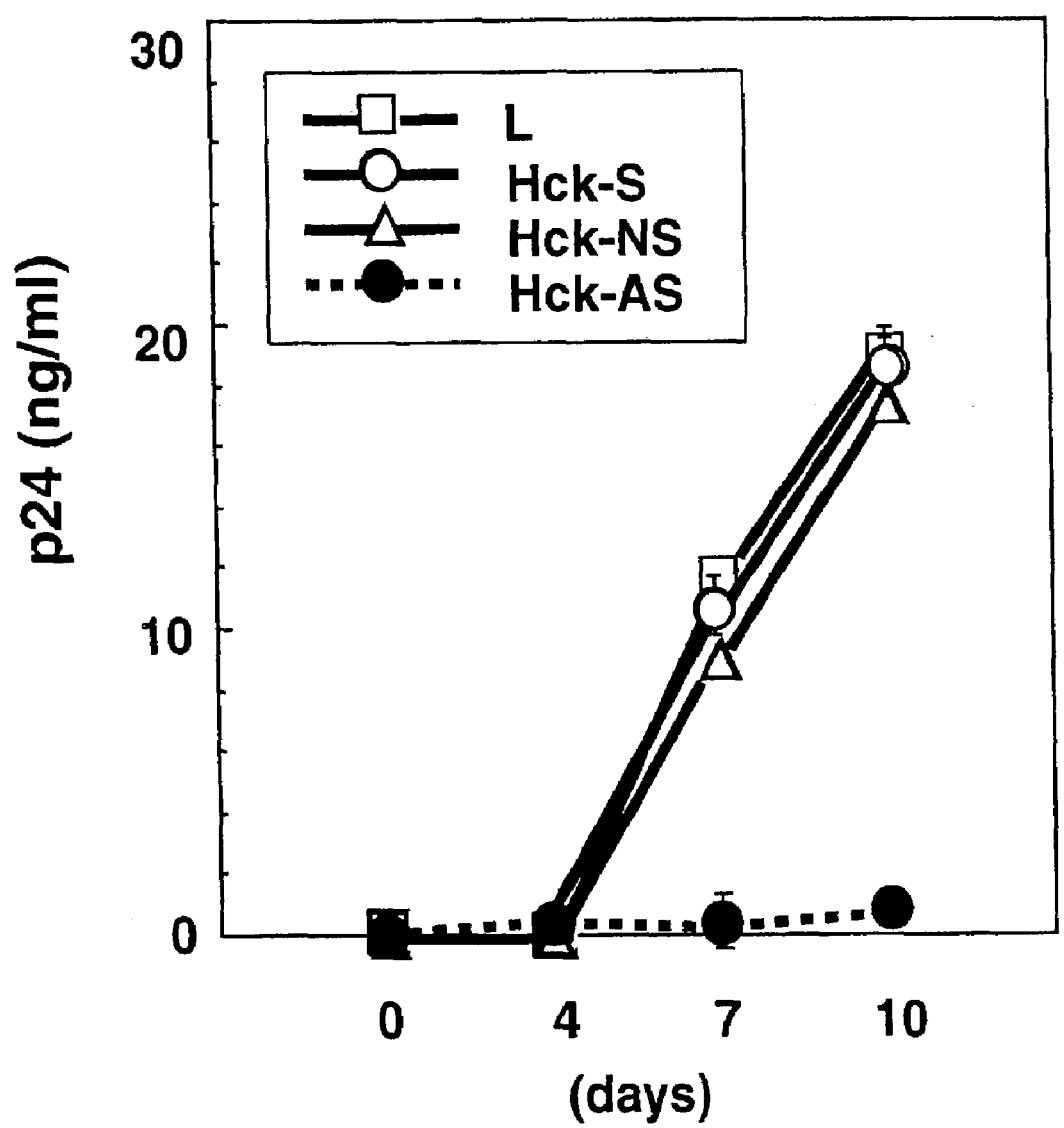
FIG. 10 shows suppression of proliferation of HIV-1 in M-MΦ treated by antisense oligonucleotide for tyrosine kinase Hck protein.
Figure 11:
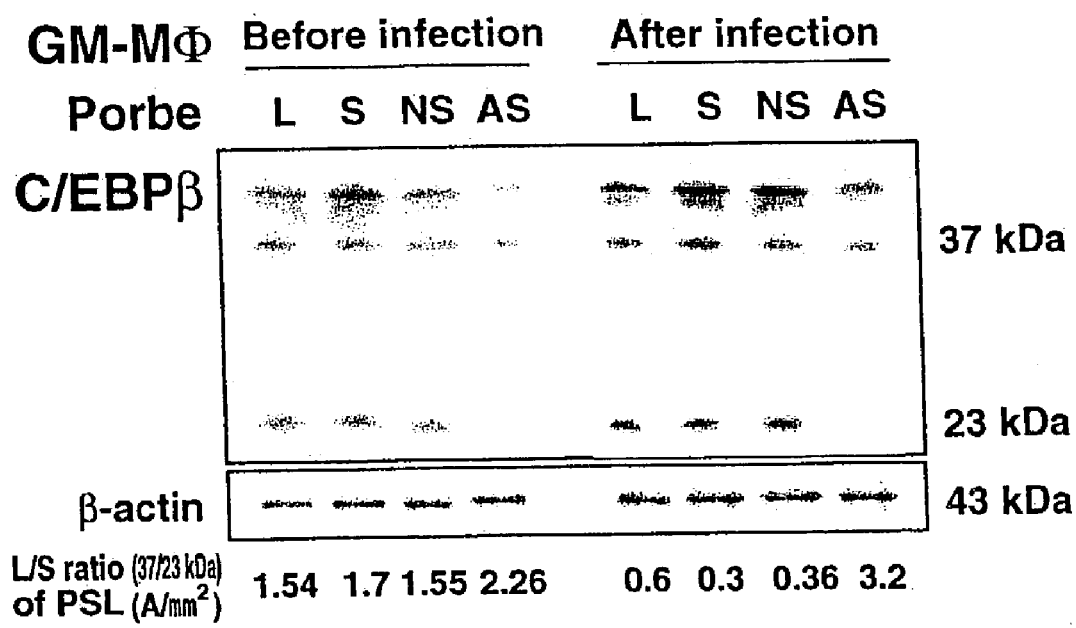
FIG. 11 shown the expression of C/EBPβ protein in GM-MΦ treated by antisense oligonucleotide for C/EBPβ protein before and after infection of HIV-1$_{BAL}$ strain.
Figure 12:
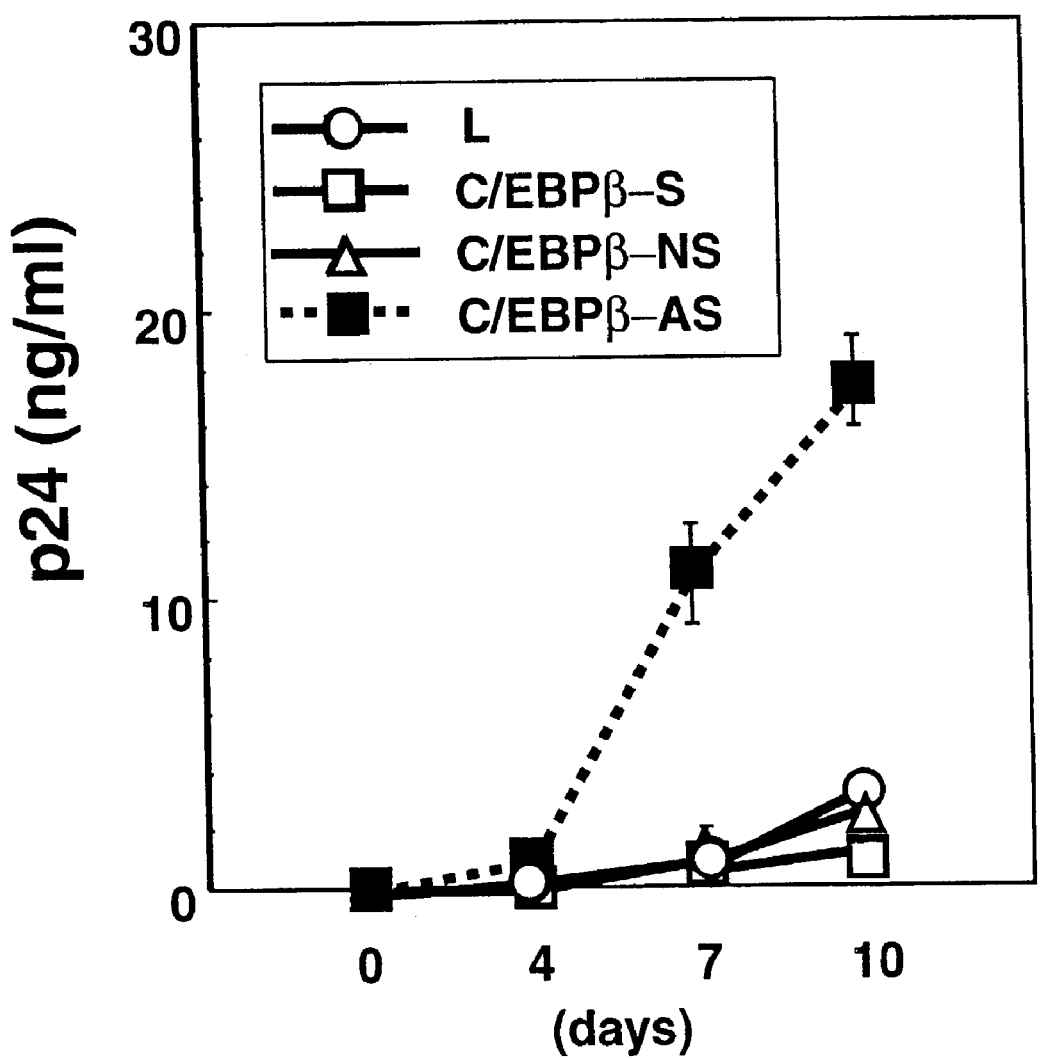
FIG. 12 shows the proliferation of HIV-1 in GM-MΦ treated by antisense oligonucleotide for C/EBPβ protein.
Figure 13:
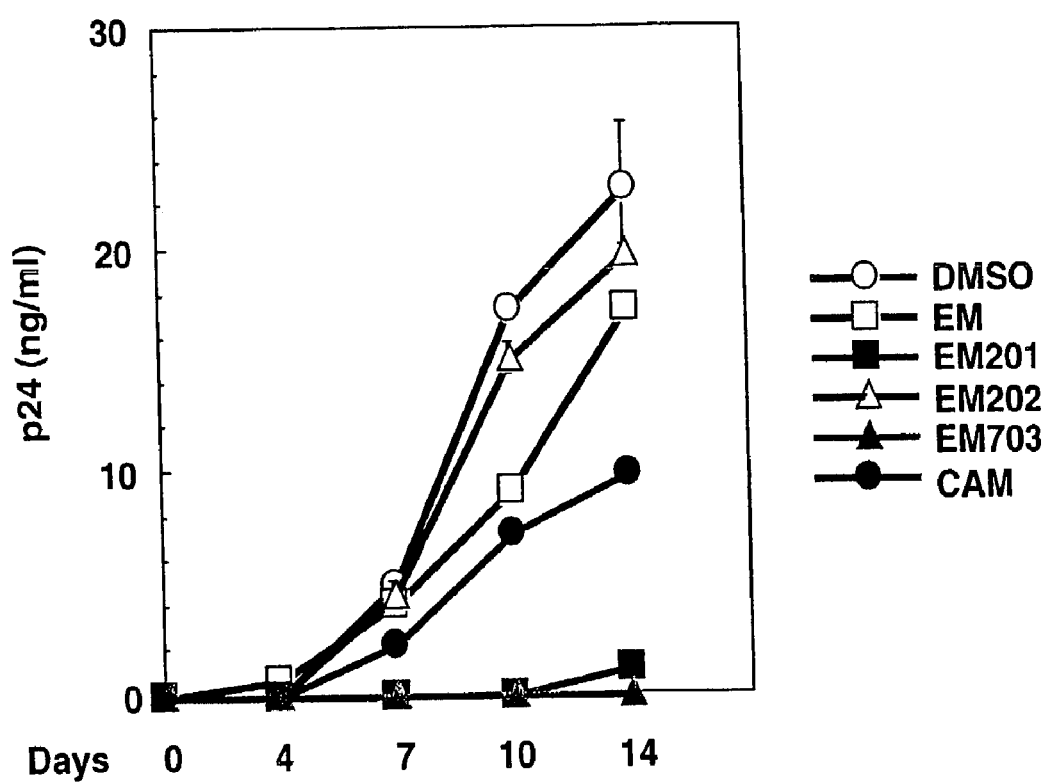
FIG. 13 shows effect of macrolide derivative on proliferation of HIV-1 in M-MΦ added with macrolide derivative such as EM, EM201, EM202, EM703 or CAM compared with addition of DMSO.
Figure 14:
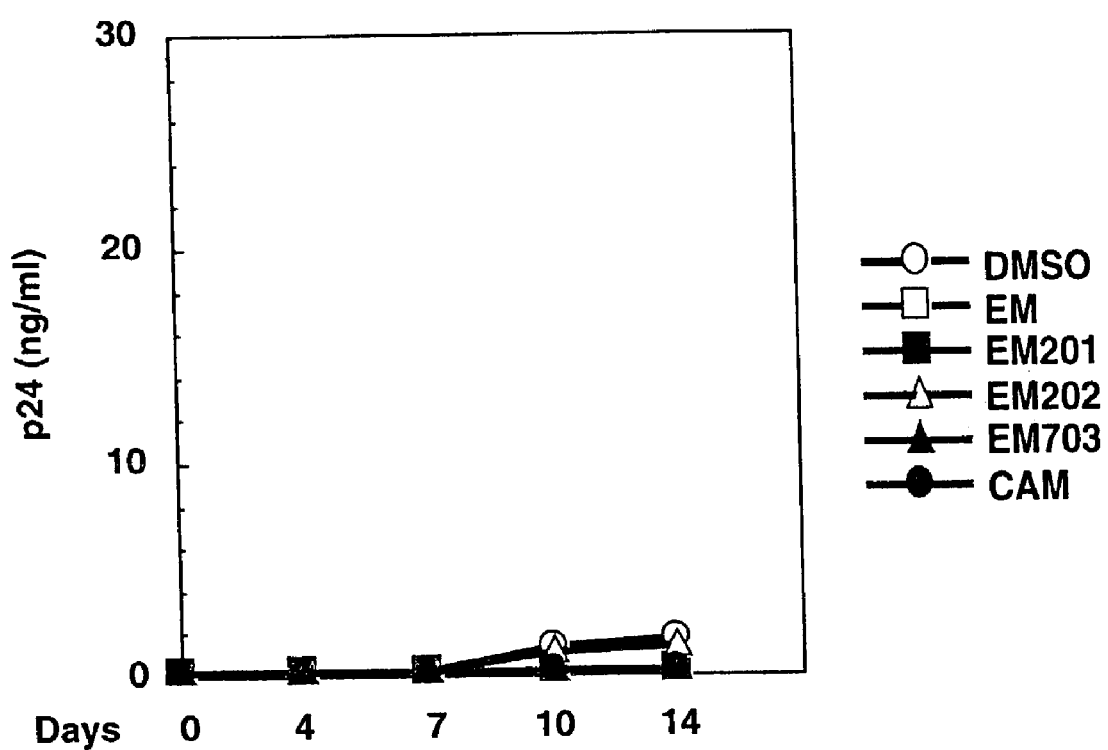
FIG. 14 shows effect of macrolide derivative on proliferation of HIV-1 in GM-MΦ added with macrolide derivative such as EM, EM201, EM202, EM703 or CAM compared with addition of DMSO.
Figure 15:
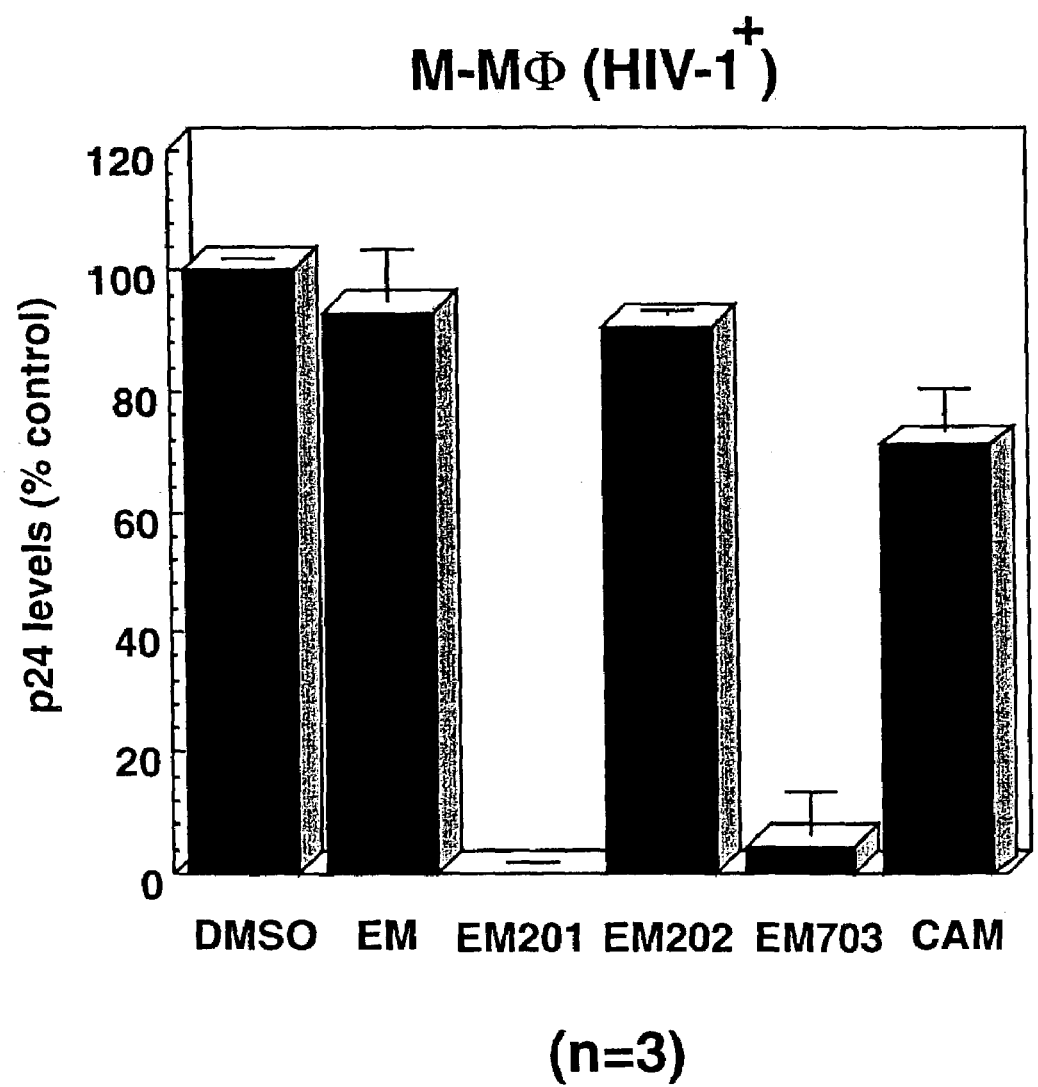
FIG. 15 shows effect of macrolide derivative on proliferation of HIV-1 in M-MΦ prepared from different humans (three subjects) added with macrolide derivatives such as EM, EM201, EM202, EM703 or CAM compared with addition of DMSO.

As compared with the control group (DMSO), in M-MΦ added with EM201 or EM703, almost no p24 was detected and viral generation was strongly suppressed on 14 days of the culture (refer to FIG. 13). In M-MΦ added with CAM, approximately ½ suppression was *recognized*, but in the group added with EM or EM202, suppression of viral generation was recognized, though not so strong as compared with EM201 and EM703 (refer to FIG. 13). In GM-MΦ, in the group added with EM, EM201, EM202, EM703 or CAM, almost no viral generation was recognized at all assay points similar to the control group (DMSO) (refer to FIG. 14). In the experiment using M-MΦ derived from human monocytes collected from three adult human volunteers, the same results as shown in FIG. 13 were obtained (refer to FIG. 15).

Figure 16:
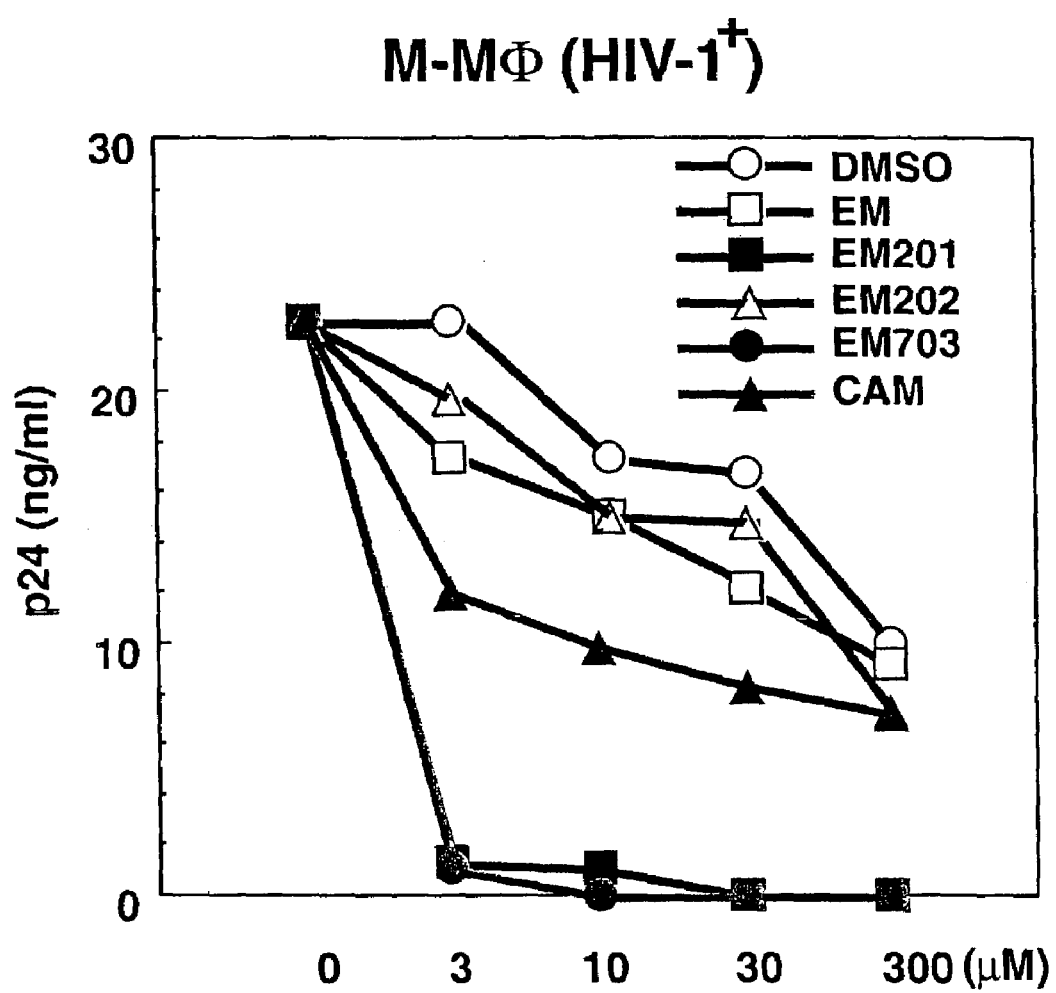
FIG. 16 shows effect of concentration of macrolide such as EM, EM201, EM202, EM703 or CAM on proliferation of HIV-1 in M-MΦ compared with addition of DMSO.

The suppressive action of EM201 and EM703 on HIV-1$_{BAL}$ in M-MΦ is concentration dependent manner and completely inhibited viral generation at 3 μM or more (refer to FIG. 16). Although viral proliferation at 300 μM was observed not only in EM201 and EM703 but also in EM, EM202 and CAM, since it was observed in the control group (DMSO), there might be due to cytotoxicity of DMSO used for dissolving agents, the future experiments were conducted at 30 μM.

EXAMPLE 2

Effect of EM, EM201, EM202, EM703 or CAM on cytopathy of HIV-1 infected M-MΦ.

Figure 17:
FIG. 17 shows effect. of macrolide derivative on cytopathy of HIV-1 infected M-MΦ added with EM, EM201, EM202, EM703 or CAM as compared with addition of DMSO.
Figure 17:
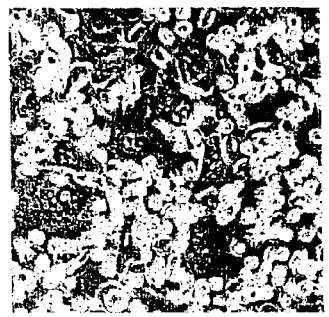
Figure 17:
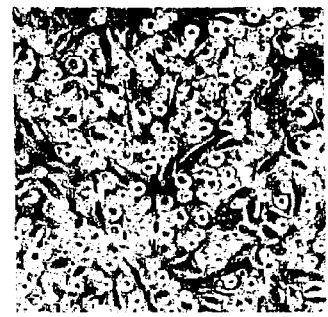
Figure 17:
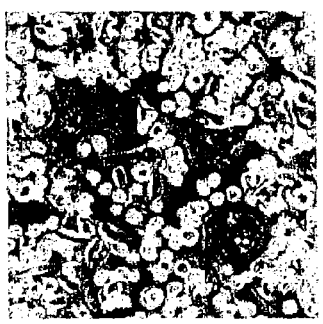
Figure 17:
Figure 17:
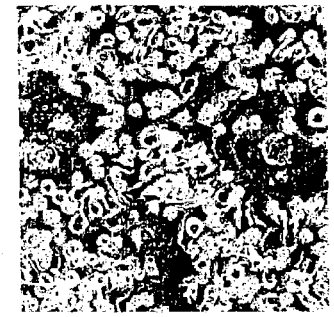

M-MΦ was subjected to contact infection with HIV-1$_{BAL}$ strain for 2 hours, added 30 μM of EM, EM201, EM202, EM703 or CAM, incubated and observed the cell morphology. In the control group (DMSO) and the group added with EM, EM202 or CAM, formation of MGC was slightly recognized in accord with increase in amount of p24 protein as shown in Example 1, but in the group added with EM201 and EM703, no cytopathic effect such as MCG formation was observed (refer to FIG. 17).

EXAMPLE 3

Effect of EM, EM201, EM202, EM703 or CAM on tyrosine kinase Hck protein of HIV-1 infected M-MΦ.

As previously described, M-MΦ expressed strongly tyrosine kinase Hck protein, and regulating the expression of tyrosine kinase Hck protein using antisense oligonucleotide could suppress proliferation of HIV-1 in M-MΦ. This result indicated that the expression of tyrosine kinase Hck protein was essential for proliferation of HIV-1 in M-MΦ. Since EM201 and EM703 suppressed proliferation of HIV-1 in M-MΦ, it was suggested that the expression of tyrosine kinase Hck protein was suppressed in M-MΦ treated with these agents.

Figure 18:
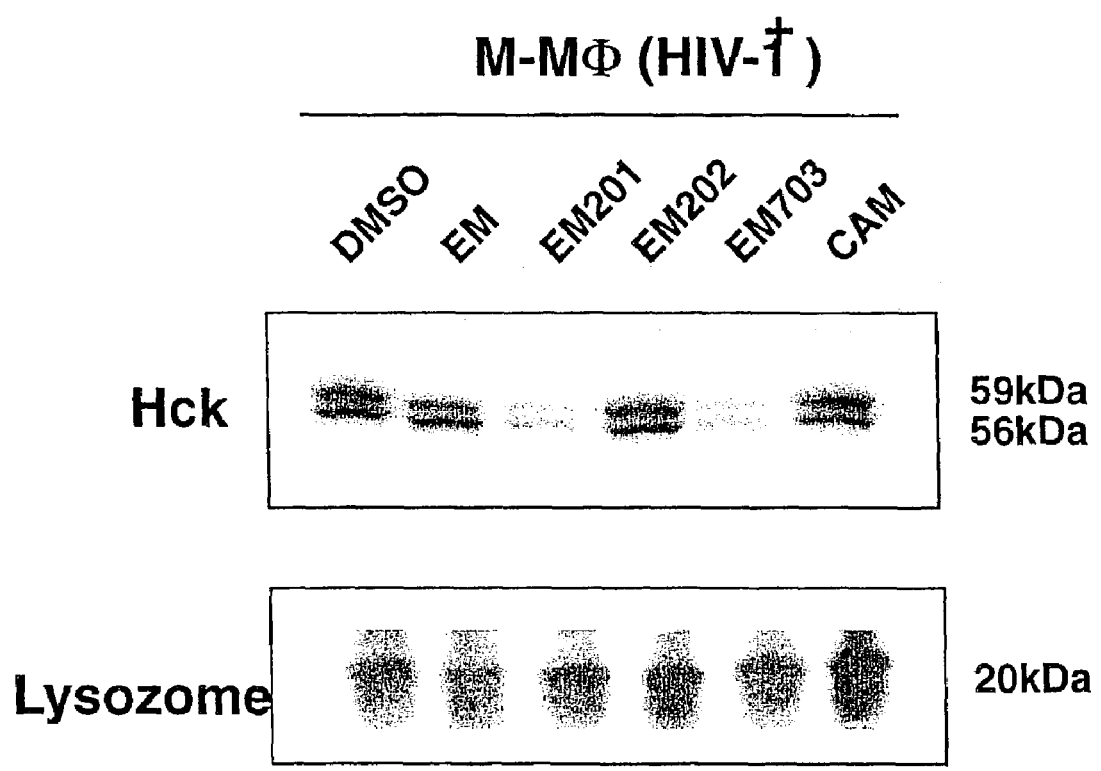
FIG. 18 shows effect of macrolide derivative such as EM, EM201, EM202, EM703 or CAM on expression of tyrosine kinase Hck protein in HIV-1 infected M-MΦ.

Consequently, M-MΦ was subjected to contact infection with HIV-1$_{BAL}$ strain for 2 hours, added 30 μM of EM, EM201, EM202, EM703 or CAM, incubated and expression of tyrosine kinase Hck protein was observed on day 2 after the infection by Western blotting. In the group of EM, EM202 and CAM, which exhibited not so strong suppressive action on viral proliferation, the suppression of tyrosine kinase Hck protein was observed, though not so strong, as compared with the control group (treated only with DMSO) (refer to FIG. 18). In EM201 and EM703, which showed strong suppressive action on viral proliferation, the expression of tyrosine kinase Hck protein was strongly suppressed (refer to FIG. 18).

EXAMPLE 4

Effect of EM, EM201, EM202, EM703 or CAM on activation of p38MAPK and ERK1/2 of HIV-1 infected M-MΦ.

The p38MAPK and ERK1/2 (p42/44MAPK) involve in various responses on intracellular signal transduction mechanism. Tyrosine phosphorylation of p38MAPK and ERK1/2 in M-MΦ infected with HIV-1$_{BAL}$ strain was examined by Western blotting. As a result, the tyrosine phosphorylation of p38MAPK was strongly induced by viral infection, but the tyrosine phosphorylation of ERK1/2 was weak. These results indicated that the activation of p38MAPK was important for viral proliferation in M-MΦ.

Consequently, effect of EM, EM201, EM202, EM703 and CAM, which have suppressive action for viral proliferation in M-MΦ, on the activation of p38MAPK and ERK1/2 was examined.

Figure 19:
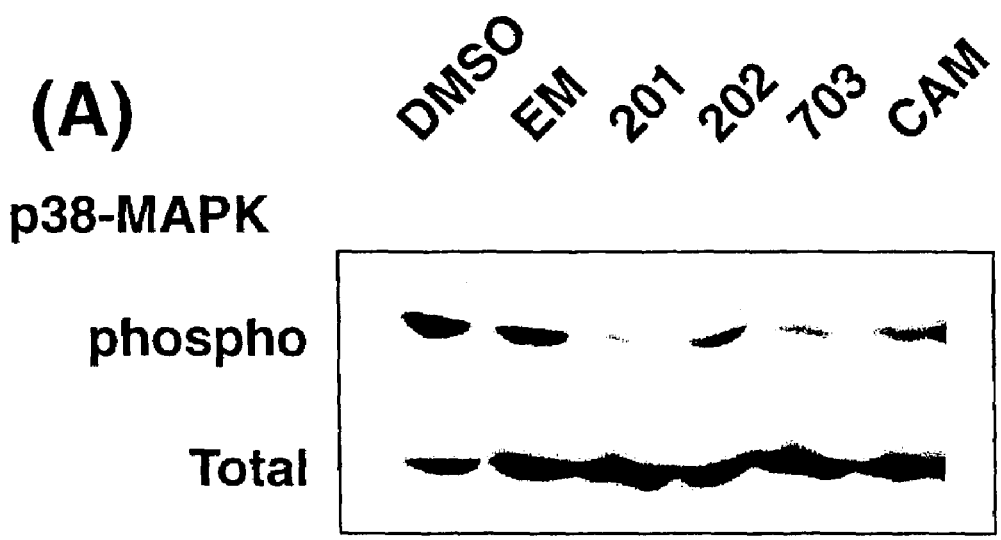
FIG. 19(A) shows effect of macrolide derivative such as EM, EM201, EM202, EM703 or CAM on activation of P38MAPK of HIV-1 infected M-MΦ as compared with DMSO, and (B) shows effect of macrolide derivative such as EM, EM201, EM202, EM703 or CAM on activation of ERK1/2 of HIV-1 infected M-MΦ as compared with DMSO.

Thirty μM of EM, EM201, EM202, EM703 or CAM were added to M-MΦ infected with HIV-1$_{BAL}$ strain, tyrosine phosphorylation of p38MAPK was detected on day 2 of the culture by Western blotting. In the group added with EM, EM202 and CAM, in which the suppressive action on viral proliferation was not so strong, the tyrosine phosphorylation of p38MAPK was recognized to decrease, though not so strong as compared with the control group (DMSO). In the group added with EM201 and EM703, which strongly suppressed viral proliferation, the tyrosine phosphorylation of p38MAPK was significantly decreased [refer to FIG. 19(A)]. In any groups, total amount of p38MAPK (total sum of phosphorylated and non-phosphorylated p38MARK) was equal. These results suggested that the suppression of viral proliferation of EM, EM201, EM202, EM703 and CAM in M-MΦ was involved in the suppression of p38MAPK.

On the other hand, in the group added with EM, EM202 and CAM, which were not so strong suppressive action of viral proliferation, tyrosine phosphorylation of ERK1/2 was weakly recognized as same in the control group (DMSO), but in the group added with EM201 and EM703, which showed strong suppressive action of viral proliferation, promotion of tyrosine phosphorylation of ERK1/2 was recognized. In any groups, total amount of ERK1/2 (total sum of phosphorylated and non-phosphorylated p38MARK) was equal [refer to FIG. 19(B)].

EXAMPLE 5

Effect of p38MAPK inhibitor on proliferation of virus in HIV-1 infected M-MΦ suppressed by addition of EM, EM201, EM202, EM703 and CAM used in the present invention.

From the results of Example 4, it was suggested that p38MAPK activation is important for proliferation of HIV-1 in M-MΦ, and the suppressive action on HIV-1 proliferation by EM, EM201, EM202, EM703 and CAM is caused by suppressive action of these substances on activation of p38MAPK.

Consequently, p38MAPK inhibitor, SB203580, (4-[4-fluoro-phenyl]-2-[4-methylsulfinylphenyl]-5-[4-pyridyl]-1H-imidazole) and ERK1/2 inhibitor, PD98059, (2-[2-amino-3-methoxyphenyl]-4H-1-benzopyran-4-one), 10 μM in concentration, were added in M-MΦ infected with HIV-1$_{BAL}$ strain and examined effect on virus.

Figure 20:
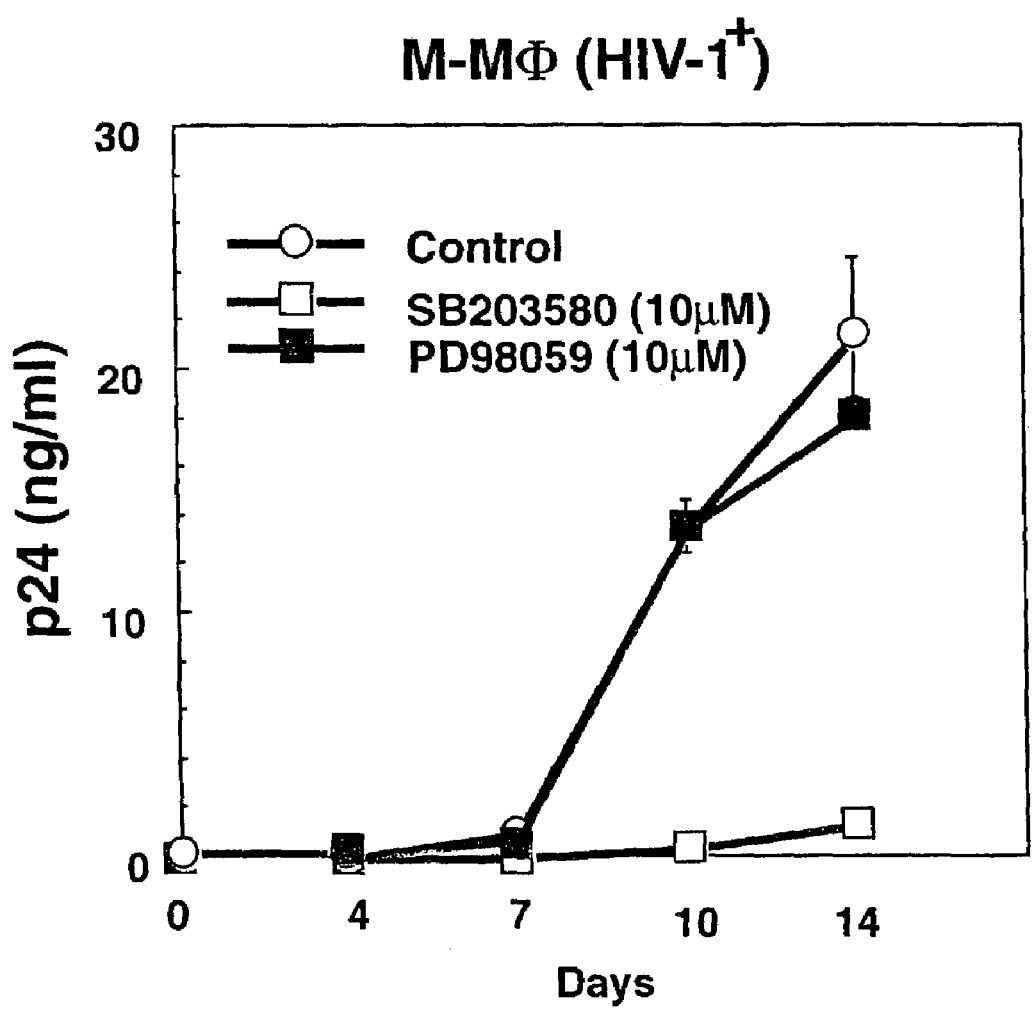
FIG. 20 shows effect of p38MAPK (SB203580) inhibitor and ERK1/2 (PD98059) inhibitor on viral proliferation of HIV-1$_{BAL}$ strain infected M-MΦ as compared with a control group.

When SB203580,10 μM, was added in M-MΦ infected with HIV-1$_{BAL}$ strain and incubated, no p24 protein was almost detected even on day 14 and proliferation of virus was inhibited (refer to FIG. 20). On the other hand, when ERK1/2 inhibitor, PD98059, 10 μM, was added, amount of p24 protein was not different in the control group and viral proliferation was recognized (refer to FIG. 20). From these experimental results, the proliferation of macrophage directed HIV-1 strain in M-MΦ essentially required activation of p38MAPK, and involvement of ERK1/2 was thought to be low.

EXAMPLE 6

Effect of EM722, EM730, EM732 and EM736 used in the present invention on proliferation of HIV-1 in M-MΦ.

M-MΦ was subjected to contact infection with HIV-1$_{BAL}$ strain for 2 hours, added various concentrations of EM722, EM730, EM732 or EM736, incubated for 10 days and amount of p24 protein in the cultured supernatant was assayed in the time-dependent manner. A group treated only with DMSO used for dissolving macrolide derivatives is set as the control group.

Figure 21:
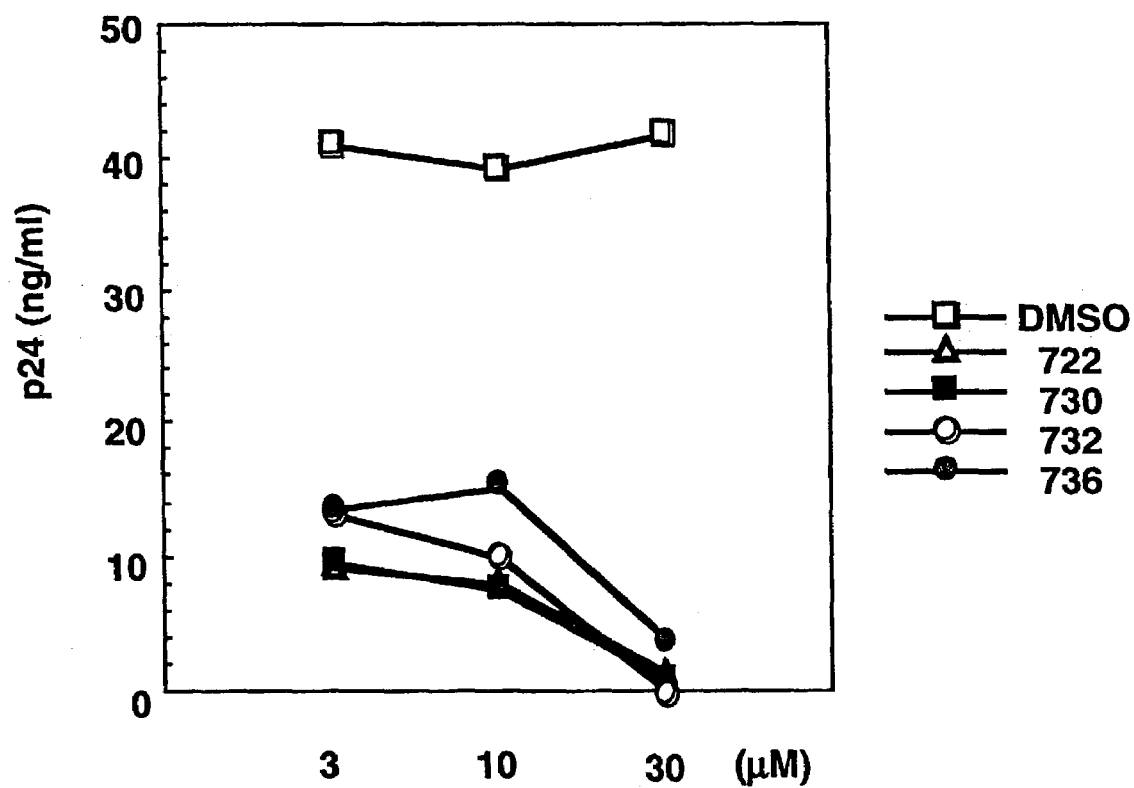
FIG. 21 shows effect of various concentration of macrolide such as EM722, EM730, EM732 or EM736 on proliferation of HIV-1 in M-MΦ as compared with DMSO.

Increase in the amount of p24 protein was observed in the cultured supernatant of the control group added only with DMSO depending on passing the culture days and proliferation of HIV-1 was recognized. However, as compared with the control group, in the group added with EM722, EM730, EM732 or EM736, production of p24 protein was suppressed depending on the concentration of agent and the suppression of viral production was recognized. Especially, in the concentration of 30 μM, any agents of EM722, EM730, EM732 and EM736 were recognized to inhibit almost completely viral production (refer to FIG. 21). In the agents, EM703, EM727, EM744, EM745, EM742, EM740, EM721, EM723, EM724, EM725, EM728, EM729, EM731, EM738, EM739, EM733, EM749 and EM726, similar results as in FIG. 21 were obtained. Further, in the experiment using M-MΦ derived from human monocytes collected from three adult healthy volunteers, the same results as in FIG. 21 were obtained.

EXAMPLE 7

Effect of EM734, EM735, EM747 and EM748 used in the present invention on proliferation of HIV-1 in M-MΦ.

M-MΦ was subjected to contact infection with HIV-1$_{BAL}$ strain for 2 hours, added various concentrations of EM734, EM735, EM747 and EM748, incubated for 10 days and amount of p24 protein in the cultured supernatant was assayed in the time-dependent manner. A group treated only with DMSO used for dissolving macrolide derivatives is set as the control group.

Figure 22:
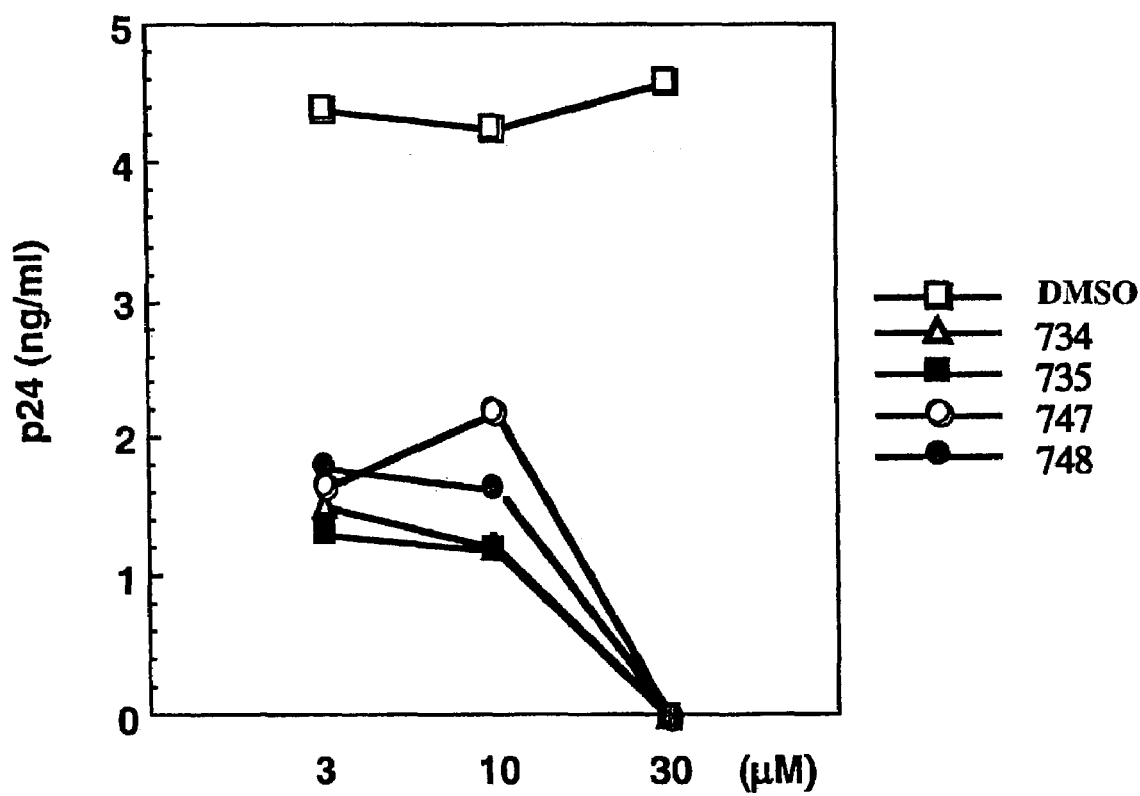
FIG. 22 shows effect of various concentration of macrolide such as EM734, EM735, EM747 or EM748 on proliferation of HIV-1 in M-MΦ as compared with DMSO.

Increase in the amount of p24 protein was observed in the cultured supernatant of the control group added only with DMSO depending on passing the culture days and proliferation of HIV-1 was recognized. However, as compared with the control group, in the group added with EM734, EM735, EM747 and EM748, production of p24 protein was suppressed depending on the concentration of agent and the suppression of viral production was recognized. Especially, in the concentration of 30 µM, any agents of EM734, EM735, EM747 and EM748 were recognized to inhibit almost completely viral production (refer to FIG. 22). Further, in the experiment using M-MΦ derived from human monocytes collected from three adult healthy volunteers, the same results as in FIG. 22 were obtained.

EXAMPLE 8

Effect of EM743 used in the present invention on proliferation of HIV-1 in M-MΦ.

M-MΦ was subjected to contact infection with HIV-1$_{BAL}$ strain for 2 hours, added various concentrations of EM743, incubated for 10 days and amount of p24 protein in the cultured supernatant was assayed in the time-dependent manner. A group treated only with DMSO used for dissolving macrolide derivatives is set as the control group.

Figure 23:
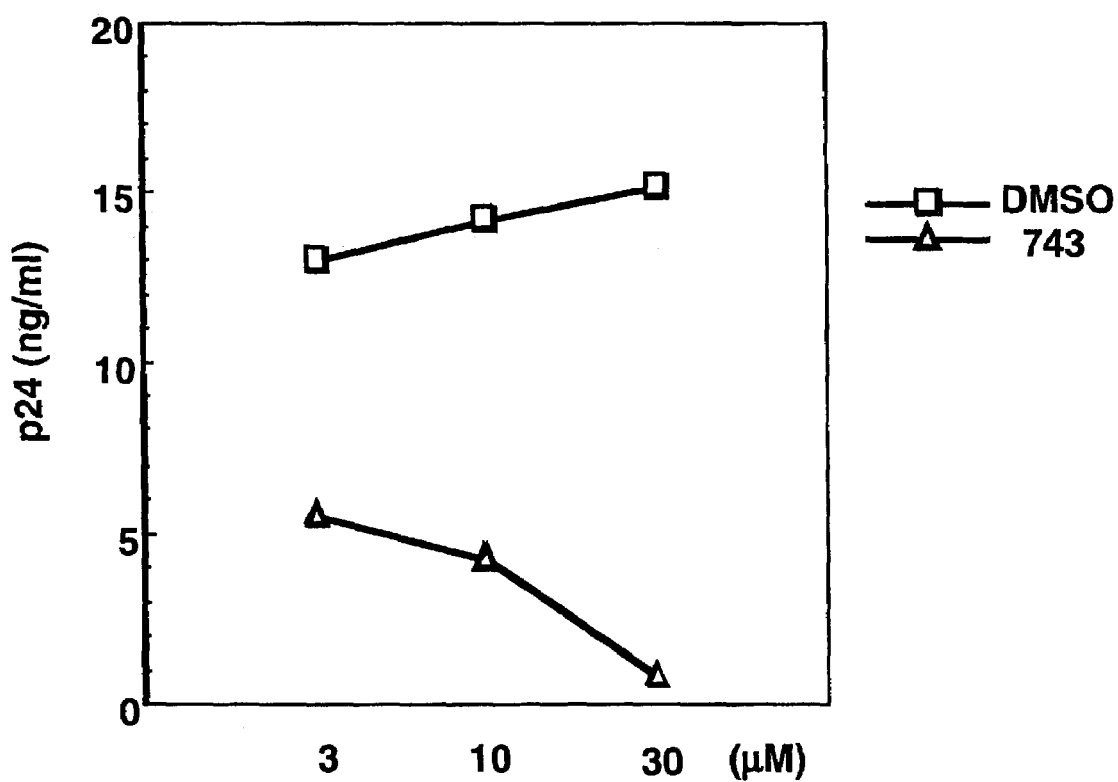
FIG. 23 shows effect of various concentration of macrolide such as EM743 on proliferation of HIV-1 in M-MΦ as compared with DMSO.

Increase in the amount of p24 protein was observed in the cultured supernatant of the control group added only with DMSO depending on passing the culture days and proliferation of HIV-1 was recognized. However, as compared with the control group, in the group added with EM743, production of p24 protein was suppressed depending on the concentration of agent and the suppression of viral production was recognized. Especially, in the concentration of 30 µM, EM743 was recognized to inhibit almost completely viral production (refer to FIG. 23). Further, in the experiment using M-MΦ derived from human monocytes collected from three adult healthy volunteers, the same result as in FIG. 23 was obtained.

EXAMPLE 9

Effect of EM746, EM750 and EM751 used in the present invention on proliferation of HIV-1 in M-MΦ.

M-MΦ was subjected to contact infection with HIV-1$_{BAL}$ strain for 2 hours, added various concentrations of EM746, EM750 and EM751, incubated for 10 days and amount of p24 protein in the cultured supernatant was assayed in the time-dependent manner. A group treated only with DMSO used for dissolving macrolide derivatives is set as the control group.

Figure 24:
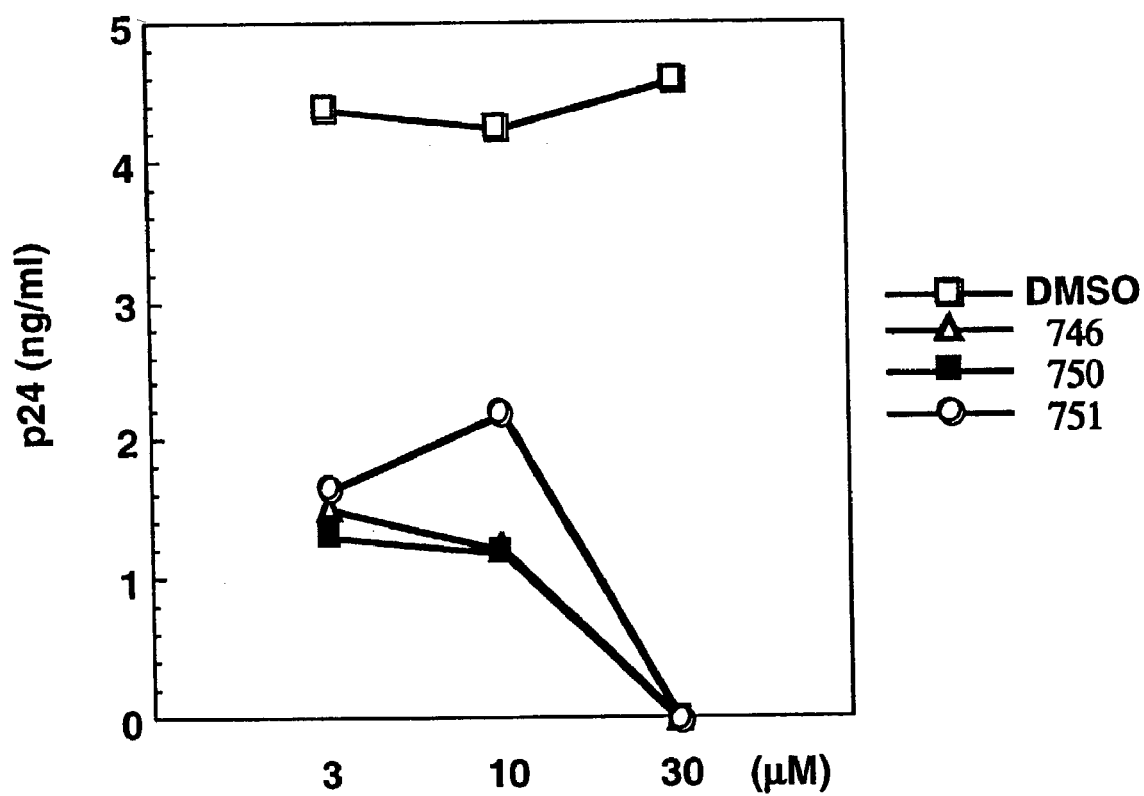
FIG. 24 shows effect of various concentration of macrolide such as EM746, EM750 or EM751 on proliferation of HIV-1 in M-MΦ as compared with DMSO.

Increase in the amount of p24 protein was observed in the cultured supernatant of the control group added only with DMSO depending on passing the culture days and proliferation of HIV-1 was recognized. However, as compared with the control group, in the group added with EM746, EM750 and EM751, production of p24 protein was suppressed depending on the concentration of agent and the suppression of viral production was recognized. Especially, in the concentration of 30 µM, any agents of EM746, EM750 and EM751 were recognized to inhibit almost completely viral production (refer to FIG. 24). Further, in the experiment using M-MΦ derived from human monocytes collected from three adult healthy volunteers, the same results as in FIG. 24 were obtained.

EXAMPLE 10

Effect of EM754 used in the present invention on proliferation of HIV-1 in M-MΦ.

M-MΦ was subjected to contact infection with HIV-1$_{BAL}$ strain for 2 hours, added various concentrations of EM754, incubated for 10 days and amount of p24 protein in the cultured supernatant was assayed in the time-dependent manner. A group treated only with DMSO used for dissolving macrolide derivatives is set as the control group.

Figure 25:
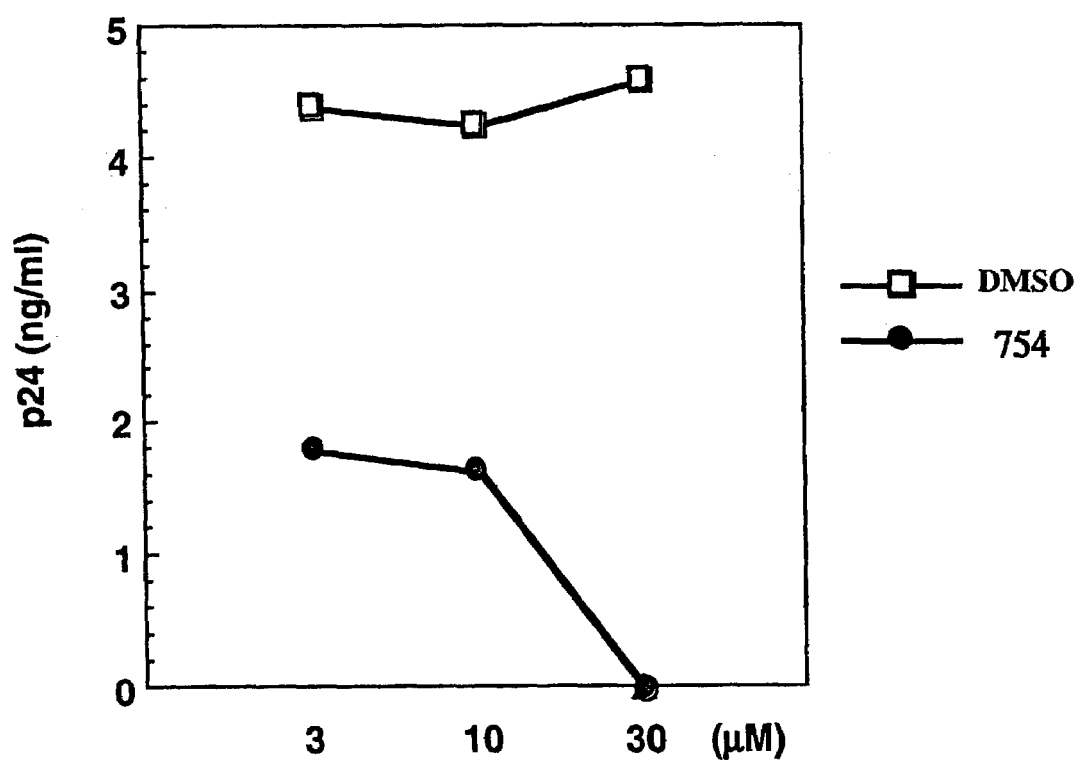
FIG. 25 shows effect of various concentration of macrolide such as EM754 on proliferation of HIV-1 in M-MΦ as compared with DMSO.

Increase in the amount of p24 protein was observed in the cultured supernatant of the control group added only with DMSO depending on passing the culture days and proliferation of HIV-1 was recognized. However, as compared with the control group, in the group added with EM7454, production of p24 protein was suppressed depending on the concentration of agent and the suppression of viral production was recognized. Especially, in the concentration of 30 µM, EM754 was recognized to inhibit almost completely viral production (refer to FIG. 25). Further, in the experiment using M-MΦ derived from human monocytes collected from three adult healthy volunteers, the same result as in FIG. 25 was obtained.

As described hereinabove, the macrolide derivatives used in the present invention were recognized to have suppressive action on macrophage directed HIV-1 proliferation in M-MΦ derived from human monocytes. Especially, EM201 and EM703, which were recognized to have action for strongly inhibiting proliferation of macrophage directed HIV-1 in M-MΦ, inhibited almost completely the proliferation of virus even at concentration of 3 µM. The suppressive action of EM201 and EM703 on the proliferation of virus was recognized to exhibit sufficient suppressive effect with 95% or more even on day 14 after the incubation by only adding EM201 or EM703 in the primary culture medium after contact infection of virus.

Further, EM, EM202 and CAM also exhibited suppression of viral production depending upon drug concentration, and the same suppressive action was recognized in EM722, EM730, EM732, EM736, EM734, EM735, EM747, EM748, EM743, EM746, EM750 EM751 and EM754, at concentration of 30,µM for almost complete inhibition. From this fact, the suppressive action was recognized to be involved in the pharmacological properties of macrolides showing accumulation in the tissue macrophage with long term acting.

As described previously, the expression of tyrosine kinase Hck protein was essential for proliferation of HIV-1 in M-MΦ, and since various macrolide derivatives of the present invention suppressed expression of tyrosine kinase Hck protein in M-MΦ, the suppressive action was suggested to be one of the mechanism of action of the suppressive action of these substances on HIV-1 proliferation. Further, since various macrolide derivatives of the present invention, which exhibit suppressive action on the proliferation of virus, inhibited tyrosine phosphorylation of p38MAPK, the suppression of HIV-1 proliferation was suggested to be based on the suppression of p38MAPK activation by these substances.

INDUSTRIAL APPLICABILITY

As described hereinabove, the present invention relates to use of macrolides derivatives for suppression of infection and proliferation of human immunodeficiency syndrome virus in the macrophage derived from the human monocytes. The present invention is not only useful as agents for suppression of infection and proliferation of human immunodeficiency syndrome virus but also expectative for clinical use as supplement agent in HAART.

REFERENCES

1): Tae-Wook Chun, Richard T. Davey Jr., Mario Ostrowski, J. Shawn Justement, Delphine Engel, James I. Mullins & Anthony S. Fauci: Relationship between pre-existing viral reservoires and the re-emergence of plasma viremia after discontinuation of highly active anti-retroviral therapy, Nat Med 6:757–761, 2000.
2): Lewis K. Schrager, M. Patricia D' Souza; Cellular and Anatomical Reservoirs of HIV-1 in Patients Receiving Potent Antiretroviral Combination Therapy, Jama 280: 67–71, 1998.
3): Swingler S, Mann A, Jacque J, Brichacek B, Sasseville V G, Williams K, Lackner A A, Janoff E N, Wang R, Fisher D, Stevenson M.: HIV-1 Nef mediates lymphocyte chemotaxis and activation By infected macrophages. Nat Med 5: 997–1003, 1999.
4): Kiyoko Akagawa, Iwao Komuro and Keiko Mochida: Diversity of macrophage derived from monocytes, Inflammation and Immunity, Vol. 8, 360–366, 2000.
5): Komuro, I., Keicho, N., Iwamoto, I., and Akagawa, K. S.: Human alvelolar macrophages and GM-CSF-induced monocyte-derived macrophages are resistant to $H_2O_2$ via their high basal- and inducible-levels of catalase activity, J. Biol. Chem. 276: 24360–24364, 2001.
6): Hashimoto, S., Komuro, I., Yamada, M. Akagawa, K. S.: IL-10 inhibits GM-CSF-dependent human monocyte survival at the early stage of the culture and inhibits the generation of macrophages, J. Immunol. 167:3619–3625, 2001.
7): Hashimoto, S., Yamada, M., Motoyoshi, K. and Akagawa, K. S.: Enhancement of macrophage-colony-stimulating factor-induced growth and differentiation of human monocytes by interleukin-10, BLOOD 89: 315–321, 1997.
8): Akagawa, K. S., Takasuka, N., Nozaki, Y., Komuro, I., Miyuki, A., Ueda, M., Naito, M. and Takahashi, K.: Generation of CD1[+] Re1B[+] Dendritic Cells and TRAP-positive Osteoclast-like Multi-nucleated Giant Cells from Human Monocytes, BLOOD 88: 4029–4039, 1996.
9): Matsuda, S., Akagawa, K., Honda, M., Yokota, Y., Takabe, Y. and Takemori, T.: Suppression of HIV replication in human monocyte-derived macrophages induced by granulocyte/macrophage colony-stimulating factor, AIDS Research and Human Retroviruses, 11: 1031–1038, 1995.
10): Inflammation and Immunity and Macrolides Up to Date, Ed. Sup. Kihachiro Shimizu and Satoshi Omura, Ed. Shoji Kudo: Iyaku Journal, Inc. Osaka, 1996.
11): Hashimoto, S., Komuro, I., Yamada, M., Akagawa, K. S.: IL-10 inhibits GM-CSF-dependent human monocyte survival at the early stage of the culture and inhibits the generation of macrophages, J. Immunol. 167: 3619–3625, 2001.
12): Nakata, K., Weiden, M., Harkin, T., Ho, D. and Rom, W. N.(1995). Low copy number and limited variability of proviral DNA in alvelolar macrophages from HIV-1-infected patients: evidence for genetic differences in HIV-1 between lung and blood macrophage populations. Mol Med 1, 744–757.
13): Kiyoko Akagawa, Iwao Komuro and Keiko Mochida: Diversity of macrophage derived from monocytes, Inflammation and Immunity, Vol. 8, 360–366, 2000. Akagawa, K. S., Takasuka, N., Nozaki, Y., Komuro, I., Miyuki, A., Ueda, M., Naito, M. and Takahashi, K: Generation of CD1[+] Re1B[+] Dendritic Cells and TRAP-positive Osteoclast-like Multi-nucleated Giant Cells from Human Monocytes, BLOOD 88:4029–4039, 1996.
14): Komuro, I., Keicho, N., Iwamoto, I., and Akagawa, K. S.: Human alvelolar macrophages and GM-CSF-induced monocyte-derived macrophages are resistant to $H_2O_2$ via their high basal- and inducible-levels of catalase activity, J. Biol. Chem. 276: 24360–24364, 2001.

The invention claimed is:

1. A method for suppressing infection and/or proliferation of human immunodeficiency syndrome virus in a macrophage derived from a human monocyte, comprising treating said macrophage with an effective amount of a macrolide derivative, wherein the macrolide derivatives is 11-(1'-hydroxypropyl)-3-[2,6-dideoxy-3-C-methyl-α-L-ribo-hexopyranosyl]oxy]-5-[3,4,6-trideoxy-3-(dimethylamino)-β-D-xylo-hexopyranosyl)oxy]-2,4,6,8,11,14-hexamethyl-10,13-15-tri-oxatricyclo[9.2.1.1.$^{9.6}$]-pentadecane-1-one or 4,13-Dioxabicyclo[8.2.1]tridec-12-en-5-one, 7-[(2,6-dideoxy-3-C-methyl-α-L-ribo-hexopyranosyl)oxy]-3-(1,2-dihydroxy-1-methylbutyl)-2,6,8,10,12-pentamethyl-9-[[3,4,6-trideoxy-3-(dimethylamino)-β-D-xylo-hexopyranosyl]oxy], and wherein the macrophage derived from human monocytes is an M type macrophage.

2. A method for suppressing infection and/or proliferation of human immunodeficiency syndrome virus in a macrophage derived from a human monocyte, comprising treating said macrophage with an effective amount of a macrolide derivative, wherein the macrolide derivatives is 11-(1'-hydroxypropyl)-3-[2,6-dideoxy-3-C-methyl-α-L-ribo-hexopyranosyl]oxy]-5-[3,4,6-trideoxy-3-(dimethylamino)-β-D-xylo-hexopyranosyl)oxy]-2,4,6,8,11,14-hexamethyl-10,13-15-tri-oxatricyclo[9.2.1.1.$^{9.6}$]-pentadecane-1-one or 4,13-Dioxabicyclo[8.2.1]tridec-12-en-5-one, 7-[(2,6-dideoxy-3-C-methyl-α-L-ribo-hexopyranosyl)oxy]-3-(1,2-dihydroxy-1-methylbutyl)-2,6,8,10,12-pentamethyl-9-[[3,4,6-trideoxy-3-(dimethylamino)-β-D-xylo-hexopyranosyl]oxy], and wherein the macrolide derivative suppresses the proliferation of the virus by suppressing expression of tyrosine kinase Hck protein and activation of p38MAPK in an M type M macrophage.

3. A method for suppressing infection and/or proliferation of human immunodeficiency syndrome virus in a macrophage derived from a human monocyte, comprising treating said macrophage with an effective amount of a macrolide derivative, wherein the macrolide derivatives is 11-(1'-hydroxypropyl)-3-[2,6-dideoxy-3-C-methyl-α-L-ribo-hexopyranosyl]oxy]-5-[3,4,6-trideoxy-3-(dimethylamino)-β-D-xylo-hexopyranosyl)oxy]-2,4,6,8,11,14-hexamethyl-10,13-15-tri-oxatricyclo[9.2.1.1.$^{9.6}$]-pentadecane-1-one or 4,13-Dioxabicyclo[8.2.1]tridec-12-en-5-one, 7-[(2,6-dideoxy-3-C-methyl-α-L-ribo-hexopyranosyl)oxy]-3-(1,2-dihydroxy-1-methylbutyl)-2,6,8,10,12-pentamethyl-9-[[3,4,6-trideoxy-3-(dimethylamino)-β-D-xylo-hexopyranosyl]oxy], and wherein said macrophage is in vitro.

4. The method according to claim 3, wherein the macrolide derivative suppresses the proliferation of the virus by suppressing expression of tyrosine kinase Hck protein and activation of p38MAPK in M type M macrophage.

5. The method according to claim 3, wherein the macrophage derived from human monocytes is an M type M macrophage.

6. The method according to claim 3, wherein the macrolide derivative suppresses the proliferation of the virus by suppressing expression of tyrosine kinase Hck protein and activation of p38MAPK in M type N macrophage.

7. A method for suppressing infection and/or proliferation of human immunodeficiency syndrome virus in a macrophage derived from a human monocyte, comprising treating said macrophage with an effective amount of a macrolide derivative, wherein the macrolide derivatives is 11-(1'-hydroxypropyl)-3-[2,6-dideoxy-3-C-methyl-α-L-ribo-hexopyranosyl]oxy]-5-[3,4,6-trideoxy-3-(dimethylamino)-β-D-xylo-hexopyranosyl)oxy]-2,4,6,8,11,14-hexamethyl-10,13-15-tri-oxatricyclo[9.2.1.1.$^{9.6}$]-pentadecane-1-one (EM201), or 4,13-Dioxabicyclo[8.2.1]tridec-12-en-5-one, 7-[(2,6-dideoxy-3-C-methyl-α-L-ribo-hexopyranosyl)oxy]-3-(1,2-dihydroxy-1-methylbutyl)- 2,6,8,10,12-pentamethyl-9-[[3,4,6-trideoxy-3-dimethylamino)-β-D-xylo-hexopyranosyl]oxy] (EM703).

8. The method according to claim 7, wherein said macrolide derivative is 11-(1'-hydroxypropyl)-3-[2,6-dideoxy-3-C-methyl-α-L-ribo-hexopyranosyl]oxy]-5-[3,4,6-trideoxy-3-(dimethylamino)-β-D-xylo-hexopyranosyl)oxy]-2,4,6,8,11,14-hexamethyl-10,13-15-tri-oxatricyclo[9.2.1.1.$^{9.6}$]-pentadecane-1-one (EM201).

9. The method according to claim 7, wherein said macrolide derivative is 4,13-Dioxabicyclo[8.2.1]tridec-12-en-5-one, 7-[(2,6-dideoxy-3-C-methyl-α-L-ribo-hexopyranosyl)oxy]-3-(1,2-dihydroxy-1-methylbutyl)-2,6,8,10,12-pentamethyl-9-[[3,4,6-trideoxy-3-dimethylamino)-β-D-xylo-hexopyranosyl]oxy](EM703).

10. The method according to claim 7, wherein said macrophage is in vitro.

* * * * *

SEQUENCE LISTING

```
<160> NUMBER OF SEQ ID NOS: 10
<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
gcttcaagta gtgtgtgccc gtctg                                         25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 2
aatcgttcta gctccctgct tgccc                                         25

<210> SEQ ID NO 3
<211> LENGTH: 25
<212> TYPE: DNA
<213> ORGANISM: Artificial Sequence
```

```
<220> FEATURE:
<223> OTHER INFORMATION: Description of Artificial Sequence: Primer

<400> SEQUENCE: 3
gtgtgactct ggtaactaga gatcc                                          25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 4
ccgcttaata ctgacgctct cgcac                                          25

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 5
ttcatcgacc ccatcctggc                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 6
gccaggatgg ggtcgatgaa                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 7
ccatatttcc cgctcgcgtg                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 8
caggcgttgc atgaacgcgg                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide probe
```

-continued

```
<400> SEQUENCE: 9
ccgcgttcat gcaacgcctg                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide probe

<400> SEQUENCE: 10
ccagagaggg cccgtgtgga                                              20
```